United States Patent
Zhu et al.

(10) Patent No.: US 9,056,857 B2
(45) Date of Patent: Jun. 16, 2015

(54) METHODS FOR TREATING OR PREVENTING CANCER AND NEURODEGENERATIVE DISEASES

(75) Inventors: Lei Zhu, Schenectady, NY (US); Yueming Li, New York, NY (US)

(73) Assignee: SLOAN-KETTERING INSTITUTE FOR CANCER RESEARCH, New York, NY (US)

( * ) Notice: Subject to any disclaimer, the term of this patent is extended or adjusted under 35 U.S.C. 154(b) by 944 days.

(21) Appl. No.: 13/140,741

(22) PCT Filed: Dec. 21, 2009

(86) PCT No.: PCT/US2009/068937
§ 371 (c)(1),
(2), (4) Date: Feb. 22, 2012

(87) PCT Pub. No.: WO2010/075255
PCT Pub. Date: Jul. 1, 2010

(65) Prior Publication Data
US 2013/0158017 A1    Jun. 20, 2013

Related U.S. Application Data

(60) Provisional application No. 61/139,751, filed on Dec. 22, 2008.

(51) Int. Cl.
| | |
|---|---|
| *A61K 31/55* | (2006.01) |
| *A61K 31/381* | (2006.01) |
| *C07D 409/12* | (2006.01) |
| *A61K 31/5513* | (2006.01) |
| *C07D 333/34* | (2006.01) |

(52) U.S. Cl.
CPC ............ *C07D 409/12* (2013.01); *A61K 31/381* (2013.01); *A61K 31/5513* (2013.01); *C07D 333/34* (2013.01)

(58) Field of Classification Search
CPC .............................. A61K 31/55; A61K 31/381
USPC .................................................. 514/221, 445
See application file for complete search history.

(56) References Cited

FOREIGN PATENT DOCUMENTS

| | | |
|---|---|---|
| WO | WO 01/70677 | 9/2001 |
| WO | WO 2007/100895 | 9/2007 |

OTHER PUBLICATIONS

International Search Report for PCT/US09/68937 (published application No. WO2010/075255) mailed Jun. 25, 2010.
Written Opinion for PCT/US09/68937 (published application No. WO2010/075255) mailed Jun. 25, 2010.
Lewis, et al., "A novel series of potent gamma-secretase inhibitors based on a benzobicyclo[4.2.1]nonane core," Bioorganic & Medicinal Chemistry Letters, 15(2): 373-378, (2005).

*Primary Examiner* — Raymond Henley, III
(74) *Attorney, Agent, or Firm* — Choate, Hall & Stewart LLP

(57) ABSTRACT

Provided are methods of treating or preventing a neurodegenerative disease comprising administering to a subject having a neurodegenerative disease an effective amount of a compound of Formula I:

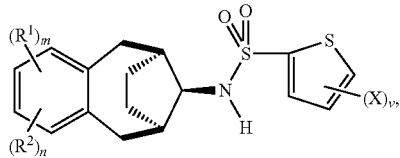

where X, $R^1$, $R^2$, subscript m, subscript n and subscript v are as defined herein.

20 Claims, No Drawings

METHODS FOR TREATING OR PREVENTING CANCER AND NEURODEGENERATIVE DISEASES

CROSS-REFERENCE TO RELATED APPLICATIONS

This application claims priority to U.S. Provisional Patent Application Ser. No. 61/139,751, filed Dec. 22, 2008, the entire content of which is incorporated herein by reference.

FIELD OF THE INVENTION

The invention relates to methods of treatment or prevention of cancer and neurodegenerative diseases comprising administering an effective amount of a Sulfonamide-Based Compound to a subject.

BACKGROUND OF THE INVENTION

Alzheimer's disease (AD) is the most prevalent form of dementia. It is a neurodegenerative disorder, clinically characterized by progressive loss of memory and general cognitive function, and pathologically characterized by the deposition of extracellular proteinaceous plaques in the cortical and associative brain regions of sufferers. These plaques mainly comprise fibrillar aggregates of beta-amyloid peptide (Aβ). Aβ is formed from amyloid precursor protein (APP). APP is a ubiquitous membrane-spanning (type 1) glycoprotein, of which three major isoforms (APP695, APP751, and APP770) are known, that undergoes a variety of proteolytic processing events (Selkoe, 1998, *Trends Cell Biol.* 8:447-453).

Generation of Aβ from APP occurs via separate intracellular proteolytic events involving the enzymes beta-secretase and γ-secretase. Beta-secretase first cleaves APP within the extracellular domain to create soluble APP-beta and beta-CTF (C-terminal fragment), which is then further processed by γ-secretase to release Aβ and γ-CTF. Given that γ-secretase cleaves beta-CTF, beta-CTF has widely been used to monitor γ-secretase activity in cell based and in vitro assays. The cleavage site of APP by γ-secretase appears to be situated within a transmembrane domain, and variability in the site of γ-secretase mediated proteolysis results in Aβ of varying chain lengths comprising heterogeneous C-termini, e.g. Aβ (1-38, "Aβ38"), Aβ (1-40, "Aβ40") and Aβ (1-42, "Aβ42"). After secretion into the extracellular medium, the initially-soluble Aβ forms aggregate, ultimately resulting in the insoluble deposits and dense neuritic plaques which are the pathological characteristics of AD. Aβ42 is more prone to aggregation than Aβ40 and is the major component of amyloid plaque (Jarrett, et al., 1993, *Biochemistry* 32:4693-4697; Kuo, et al., 1996, *J. Biol. Chem.* 271:4077-4081).

Alternatively, APP can be sequentially cleaved by alpha-secretase and γ-secretase to produce soluble APP-alpha, P3 and γ-CTF. Alpha-secretase cleavage precludes the formation of Aβ peptides.

Various interventions in the plaque-forming process have been proposed as therapeutic treatments for AD (see, e.g., Hardy and Selkoe, 2002, *Science* 297:353-356). One such method of treatment that has been proposed is that of blocking or attenuating the production of Aβ, for example, by inhibition of beta- or γ-secretase. Other proposed methods of treatment include administering a compound(s) which blocks the aggregation of Aβ, or administering an antibody which selectively binds to Aβ. Activation of α-secretase is also an appealing strategy for the development of AD therapy, in that increased alpha-secretase cleavage might lend to lessened Aβ generation.

γ-secretase is a macromolecular aspartyl protease composed of at least four proteins: presenilin (PS), nicastrin (NCT), PEN-2 and APH-1 (De Strooper, 2003, *Neuron* 38:9-12). Recently, CD147 and TMP21 have been found to be associated with the γ-secretase complex (Chen, et al., 2006, *Nature* 440:1208-1212; Zhou et al., 2005, *Proc. Natl. Acad. Sci. USA*, 102:7499-7504). Among these known components, PS is believed to contain the active site of γ-secretase (Esler et al., 2000, *Nat. Cell. Biol.*, 2:428:434; Li et al., 2000, *Nature* 405:689-694; Wolfe et al., 1999, *Nature* 398:513-517). Considerable effort has been made to understand the process of γ-secretase substrate recognition and its catalytic machinery. A PS-dependent protease can process any single-pass transmembrane (TM) protein regardless of its primary sequence as long as the TM protein extracellular domain is smaller than 300 amino acids. Moreover, the size of the extracellular domain appears to determine the efficiency of substrate cleavage (Struhl and Adachi, 2000, *Mol. Cell.* 6:625-636).

The sequential cleavage of APP by two proteases (beta- or alpha-secretase followed γ-secretase) is analogous to a recently defined signaling paradigm, known as regulated intramembrane proteolysis (RIP) (Brown et al., 2000, *Cell* 100:391-398). RIP generally requires two proteolytic steps to initiate its signaling cascade, whereby the second intramembrane cleavage is dependent on the first cleavage. Indeed, Notch, a type I transmembrane protein employs RIP and is a substrate for γ-secretase cleavage. Activation of Notch (which is γ-secretase dependent) has been implicated in cancer development. As such, inhibitors of γ-secretase activity might not only have implications in the treatment of AD, but may also have benefit in treatment of all diseases in which γ-secretase plays a role.

Cancer also affects a significant number of people. It is currently believed that the Notch signaling pathway is implicated in cancer biology. The Notch signaling pathway involves cell-cell communication, and aberrant Notch signaling has been observed in cancer cells. Such aberrant Notch signaling has been linked to tumor formation. γ-Secretase inhibitors have been found to prevent the generation of the active domain of Notch molecules, thereby suppressing Notch signaling.

There is a need in the art for additional treatments for cancer and neurodegenerative diseases, such as Alzheimer's disease.

SUMMARY OF THE INVENTION

In one embodiment, the invention provides methods for treating or preventing cancer, comprising administering to a subject an effective amount of a compound of the following Formula I

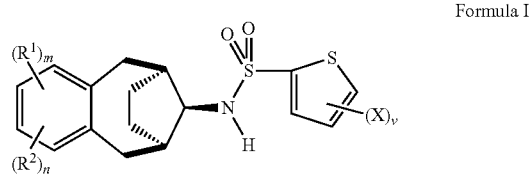

Formula I or a pharmaceutically acceptable salt thereof, wherein:
X is H, halo, $C_1$-$C_6$ alkyl, $C_1$-$C_6$ haloalkyl, $C_1$-$C_6$ alkoxy, or cyano;
each $R^1$ is independently H, halo, $C_1$-$C_6$ alkyl, $C_1$-$C_6$ haloalkyl, $C_1$-$C_6$ alkoxy, or cyano;
$R^2$ is

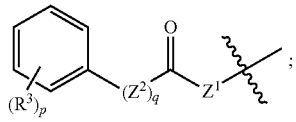

each $R^3$ is independently H, halo, $C_1$-$C_6$ alkyl, $C_1$-$C_6$ haloalkyl, $C_1$-$C_6$ alkoxy, or cyano;
$Z^1$ is NH, O, or $CH_2$;
$Z^2$ is —($C_1$-$C_6$ alkylene)-, —($C_2$-$C_6$ alkenylene)-, —(NH—($C_1$-$C_6$ alkylene))- or —(O—($C_2$-$C_6$ alkylene))-;
m is 3;
n is 1;
p is an integer from 1 to 5;
q is 0 or 1; and
v is an integer from 1 to 3.

In another embodiment, the invention provides methods for treating or preventing cancer, comprising administering to a subject an effective amount of a compound of the following Formula II Formula II

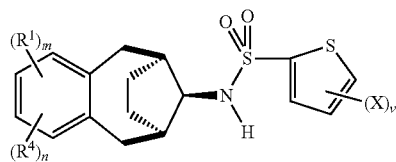

or a pharmaceutically acceptable salt thereof, wherein:
X is H, halo, $C_1$-$C_6$ alkyl, $C_1$-$C_6$ haloalkyl, $C_1$-$C_6$ alkoxy, or cyano;
each $R^1$ is independently H, halo, $C_1$-$C_6$ alkyl, $C_1$-$C_6$ haloalkyl, $C_1$-$C_6$ alkoxy, or cyano;
$R^4$ is

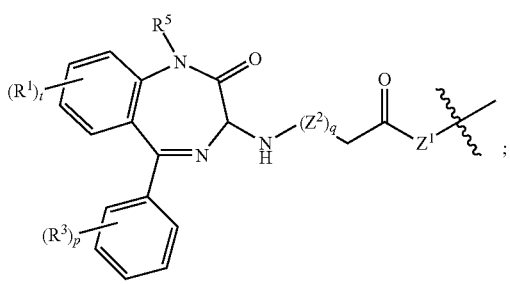

each $R^3$ is independently H, halo, $C_1$-$C_6$ alkyl, $C_1$-$C_6$ haloalkyl, $C_1$-$C_6$ alkoxy, or cyano;
$R^5$ is H, $C_1$-$C_6$ alkyl, or $C_1$-$C_6$ haloalkyl;
$Z^1$ is NH, O, or $CH_2$;
$Z^2$ is —($C_1$-$C_6$ alkylene)- or —($C_2$-$C_6$ alkenylene)-;
m is 3;
n is 1;
p is 5;

t is 4;
q is 0 or 1; and
v is an integer from 1 to 3.

In one embodiment, the invention provides methods for treating or preventing a neurodegenerative disease, comprising administering to a subject an effective amount of a compound of the following Formula I Formula I

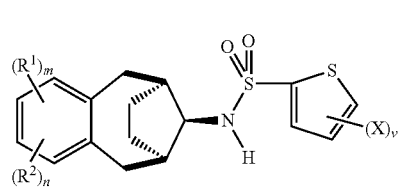

or a pharmaceutically acceptable salt thereof, wherein:
X is H, halo, $C_1$-$C_6$ alkyl, $C_1$-$C_6$ haloalkyl, $C_1$-$C_6$ alkoxy, or cyano;
each $R^1$ is independently H, halo, $C_1$-$C_6$ alkyl, $C_1$-$C_6$ haloalkyl, $C_1$-$C_6$ alkoxy, or cyano;
$R^2$ is

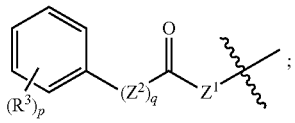

each $R^3$ is independently H, halo, $C_1$-$C_6$ alkyl, $C_1$-$C_6$ haloalkyl, $C_1$-$C_6$ alkoxy, or cyano;
$Z^1$ is NH, O, or $CH_2$;
$Z^2$ is —($C_1$-$C_6$ alkylene)-, —($C_2$-$C_6$ alkenylene)-, —(NH—($C_1$-$C_6$ alkylene))- or —(O—($C_2$-$C_6$ alkylene))-;
m is 3;
n is 1;
p is an integer from 1 to 5;
q is 0 or 1; and
v is an integer from 1 to 3.

In another embodiment, the invention provides methods for treating or preventing a neurodegenerative disease, comprising administering to a subject an effective amount of a compound of the following Formula II Formula II

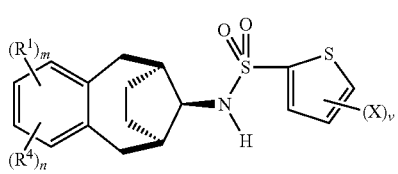

or a pharmaceutically acceptable salt thereof, wherein:
X is H, halo, $C_1$-$C_6$ alkyl, $C_1$-$C_6$ haloalkyl, $C_1$-$C_6$ alkoxy, or cyano;
each $R^1$ is independently H, halo, $C_1$-$C_6$ alkyl, $C_1$-$C_6$ haloalkyl, $C_1$-$C_6$ alkoxy, or cyano;

$R^4$ is

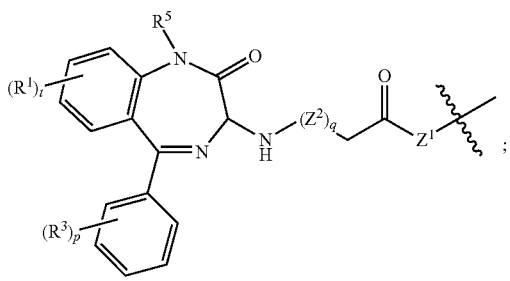

each $R^3$ is independently H, halo, $C_1$-$C_6$ alkyl, $C_1$-$C_6$ haloalkyl, $C_1$-$C_6$ alkoxy, or cyano;

$R^5$ is H, $C_1$-$C_6$ alkyl, or $C_1$-$C_6$ haloalkyl;

$Z^1$ is NH, O, or $CH_2$;

$Z^2$ is —($C_1$-$C_6$ alkylene)- or —($C_2$-$C_6$ alkenylene)-;

m is 3;

n is 1;

p is 5;

t is 4;

q is 0 or 1; and v is an integer from 1 to 3.

DETAILED DESCRIPTION OF THE INVENTION

I. Definitions

The following definitions are used in connection with the Sulfonamide-Based Compounds:

The term "$C_1$-$C_6$ alkyl," as used herein unless otherwise defined, refers to a straight chain or branched non-cyclic hydrocarbon having from 1 to 6 carbon atoms, wherein one of the hydrocarbon's hydrogen atoms has been replaced by a single bond. Representative straight chain $C_1$-$C_6$ alkyls include -methyl, -ethyl, -n-propyl, n-butyl, -n-pentyl, and n-heptyl. Representative branched $C_1$-$C_6$ alkyls include -isopropyl, -sec-butyl, -isobutyl, -tert-butyl, -isopentyl, -neopentyl, 1-methylbutyl, 2-methylbutyl, 3-methylbutyl, 1,1-dimethylpropyl and 1,2-dimethylpropyl.

The term "$C_1$-$C_6$ haloalkyl," as used herein unless otherwise defined, refers to a $C_1$-$C_6$ alkyl, as defined above, wherein one or more of the —$C_1$-$C_6$ alkyl's hydrogen atoms has been replaced with —F, —Cl, —Br, or —I. Representative examples of a $C_1$-$C_6$ haloalkyl include, but are not limited to —$CCl_3$, —$CF_3$, —$CI_3$, —$CBr_3$, —$CHCl_2$, —$CHF_2$, —$CHI_2$, —$CHBr_2$, —$CH_2Cl$, —$CH_2Br$, —$CH_2F$, —$CH_2I$, —$CH_2CH_2Br$, —$CH_2CH_2I$, —$CH_2CH_2F$, —$CH_2CH_2Cl$, —$CH_2CH_2CH_2Br$, —$CH_2CH(Br)CH_3$, —$CH_2CH_2CH_2Cl$, —$CH_2CH_2CH_2F$, —$CH_2CH_2CH_2I$, —$CH_2CH_2CH_2CH_2Br$, —$CH_2CH_2CH_2CH_2Cl$, —$CH_2CH(Cl)CH_2CH_3$, —$CH_2CH_2CH_2CH_2F$, —$CH(F)CH_2CH_2CH_3$, —$CH_2CH_2CH_2CH_2I$, —$CH_2CH_2CH_2CH_2CH_2Br$, —$CH_2CH_2CH_2CH_2CH_2Cl$, —$CH_2CH_2CH_2CH_2CH_2F$, —$CH_2CH_2CH_2CH_2CH_2I$, —$CH_2CH_2CH_2CH_2CH_2CH_2Br$, —$CH_2CH_2CH_2CH_2CH_2CH_2Cl$, $CH_2CH_2CH_2CH_2CH_2CH_2F$, —$CH_2CH_2CH_2CH_2CH_2CH_2I$, and —$CH_2CH_2CH(I)CH_2CH_2CH_3$.

The term "$C_1$-$C_6$ alkoxy," as used herein unless otherwise defined, refers to —O—($C_1$-$C_6$ alkyl), wherein $C_1$-$C_6$ alkyl is as defined above. Representative examples of a $C_1$-$C_6$ alkoxy include, but are not limited to, —$OCH_3$, —$OCH_2CH_3$, —$OCH_2CH_2CH_3$, —$OCH(CH_3)CH_3$, —$OCH_2CH_2CH_2CH_3$, —$OCH_2CH(CH_3)CH_3$, —$OCH(CH_3)CH_2CH_3$, —$OC(CH_3)_3$, —$OCH_2CH_2CH_2CH_2CH_3$, —$OCH_2CH(CH_3)CH_2CH_3$, —$OCH_2CH_2CH_2CH_2CH_2CH_3$, and —$OCH_2CH_2CH(CH_3)CH_2CH_3$.

The term "$C_1$-$C_6$ alkylene," refers to a $C_1$-$C_6$ alkyl where a hydrogen atom of the $C_1$-$C_6$ alkyl's terminal —$CH_3$ group is replaced with a bond. Representative examples of a $C_1$-$C_6$ alkylene include, but are not limited to, —$CH_2$—, —$CH_2CH_2$—, —$CH_2CH_2CH_2$—, —$CH(CH_3)CH_2$—, —$CH_2CH_2CH_2CH_3$—, —$CH_2CH(CH_3)CH_2$—, —$CH(CH_3)CH_2CH_2$—, —$CH_2CH_2CH_2CH_2$—, —$CH_2CH(CH_3)CH_2CH_2$—, —$CH_2CH_2CH_2CH_2CH_2$—, and —$CH_2CH_2CH(CH_3)CH_2CH_2$—.

The term "$C_2$-$C_6$ alkenylene," refers to a $C_2$-$C_6$ alkylene, as defined above, but having one or more carbon-carbon double bonds. Representative examples of a $C_2$-$C_6$ alkenylene include, but are not limited to —HC=CH—, —HC=CH—$CH_2$—, —HC=CH—$CH_2$—$CH_2$—, —$CH_2$—HC=CH—$CH_2$—, —HC=CH—$CH_2$—$CH_2$—$CH_2$—, —$CH_2$—$CH_2$—HC=CH—$CH_2$—, —HC=CH—$CH_2$—$CH_2$—$CH_2$—$CH_2$—, and —$CH_2$—HC=CH—$CH_2$—$CH_2$—$CH_2$—.

The term "halo," as used herein unless otherwise defined, refers to —F, —Cl, —Br or —I.

The term "subject," as used herein unless otherwise defined, is a mammal, e.g., a human, mouse, rat, guinea pig, dog, cat, horse, cow, pig, or non-human primate, such as a monkey, chimpanzee, or baboon. In one embodiment, the subject is a human.

The term "pharmaceutically acceptable salt," as used herein unless otherwise defined, is a salt of a basic group, such as an amino group, on the Sulfonamide-Based Compounds. Illustrative salts of a basic group include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate, camphorsulfonate, and pamoate (i.e., 1,1'-methylene-bis-(2-hydroxy-3-naphthoate)) salts.

An "effective amount" when used in connection with a Sulfonamide-Based Compound is an amount that is effective for treating or preventing cancer or a neurodegenerative disease.

An "effective amount" when used in connection with another anti-cancer agent is an amount that is effective for treating or preventing cancer alone or in combination with a Sulfonamide-Based Compound. An "effective amount" when used in connection with another anti-neurodegenerative disease agent is an amount that is effective for treating or preventing a neurodegenerative disease alone or in combination with a Sulfonamide-Based Compound. "In combination with" includes administration within the same composition and via separate compositions; in the latter instance, the other anti-neurodegenerative disease agent is effective for treating or preventing a neurodegenerative disease during a time when the Sulfonamide-Based Compound exerts its prophylactic or therapeutic effect, or vice versa, and the other anti-cancer agent is effective for treating or preventing cancer during a time when the Sulfonamide-Based Compound exerts its prophylactic or therapeutic effect, or vice versa.

The language "substantially free of its corresponding opposite enantiomer" means having no more than about 10 mol %, in another embodiment no more than about 5 mol %, in another embodiment no more than about 2 mol %, in another embodiment no more than about 1 mol %, in another embodiment no more than about 0.5 mol % and in another embodiment no more than about 0.1 mol %, of its corresponding opposite enantiomer.

As used herein, the term "amyloid precursor protein" ("APP") refers to an integral membrane protein that is expressed in tissues and concentrated in the synapses of neurons. As used herein, the term APP is meant to encompass all isoforms and forms of APP, both wild-type and synthetic. Exemplary APP isoforms include, but are not limited to, APP695, the 695 amino acid splice variant of APP (see GenBank accession no. Y00264 and Kang, et al., 1987, *Nature* 325:733-736), APP 751, the 751 amino acid splice variant of APP (see Ponte, et al., 1988, *Nature* 331:525-527), and APP770, the 770 amino acid splice variant of APP (see Kitaguchi, et al., 1988, *Nature* 331:530-532). Other isoforms of APP include APP714, L-APP752, L-APP733, L-APP696, L-APP677, APP563 and APP365. Use of the term APP herein is meant to include all isoforms containing mutations found in familial AD and other amyloidosis conditions. For example, these mutations include, but are not limited to, the Swedish double mutation (Lys670Asn, Met671 Leu); the London mutation (Val717Ile); the Indiana mutation (Val717Leu); naturally occurring mutations including Val717Phe, Val717Gly, Ala713Thr, and Ala713Val; the Austrian mutation (Thr714Ile); the Iranian mutation (Thr714Ala); the French mutation (Val715Met); the German mutation (Val715Ala); the Florida mutation (Ile716Val); the Australian mutation (Leu723Pro); the Flemish mutation (Ala692Gly); the Dutch mutation (Glu693Gln); the Arctic mutation (Glu693Gly); the Italian mutation (Glu693Lys); the Iowa mutation (Asp694Asn); and the amyloidosis-Dutch type mutation (Glu693Gln). (All numbering herein is relative to the APP770 form). Use of the term APP herein further includes proteins containing one or more additions, deletions, insertions, or substitutions relative to the isoforms described above, and APP proteins from humans and other species. Unless a specific isoform is specified, APP when used herein generally refers to any and all isoforms of APP, with or without mutations, from any species.

As used herein, the term "amyloid-beta ("Aβ")" refers to a peptide derived from the proteolytic cleavage of APP. Cleavage of Aβ by beta-secretase generates two APP fragments, referred to herein as "beta-CTF" and "soluble beta-APP." Beta-CTF is an approximately 100 amino acid fragment, wherein the N-terminus of beta-CTF defines the N-terminus of Aβ. An example of a naturally occurring beta-CTF sequence is the beta-CTF of APP695. Derivatives of the beta-CTF portion of APP are well known in the art (see, e.g., Lichtenthaler, et al., 1997, *Biochemistry* 36:15396-15403; and Selkoe, 1999, *Nature* 399:A23-A31). Such derivatives can themselves provide a beta-CTF domain or can serve as a starting point for creating additional derivatives. Subsequent γ-secretase cleavage of beta-CTF generates the C-terminus of Aβ. Because γ-secretase cleavage of the beta-CTF fragment occurs over a short stretch of amino acids rather than at a single peptide bond, Aβ ranges in size from, e.g., 39 to 43 peptides. However, Aβ peptides of 40 and 42 amino acids in length ("Aβ40" and "Aβ42," respectively) predominate.

As used herein, the term "γ-secretase" refers to an enzyme(s) with the ability to cleave at the γ-secretase site of a protein having a γ-secretase cleavage site, e.g., APP. As used herein, γ-secretase includes all recombinant forms, mutations, and other variants of γ-secretase so long as these maintain a functional capability to catalyze the cleavage of molecules or substrates bearing γ-secretase cleavage sites.

As used herein, the term "about" or "approximately," when used in conjunction with a number, refers to any number within 1, 5 or 10% of the referenced number.

As used herein, the term "elderly human" refers to a human 65 years or older.

As used herein, the term "human adult" refers to a human that is 18 years or older.

As used herein, the term "human child" refers to a human that is 1 year to 18 years old.

As used herein, the term "human toddler" refers to a human that is 1 year to 3 years old.

As used herein, the term "human infant" refers to a newborn to 1 year old year human.

As used herein, the term "premature human infant" refers to a human infant born at less than 37 weeks of gestational age.

Concentrations, amounts, percentages and other numerical values may be presented herein in a range format. It is to be understood that such range format is used merely for convenience and brevity and should be interpreted flexibly to include not only the numerical values explicitly recited as the limits of the range but also to include all the individual numerical values or sub-ranges encompassed within that range as if each numerical value and sub-range is explicitly recited.

II. Sulfonamide-Based Compounds of Formulas I and II

In accordance with the invention, a compound or pharmaceutically acceptable salt of the compound of Formula I or II set forth above (a "Sulfonamide-Based Compound") is useful for treating or preventing cancer or a neurodegenerative disease.

In one embodiment, the Sulfonamide-Based Compounds are compounds of the following Formula I.

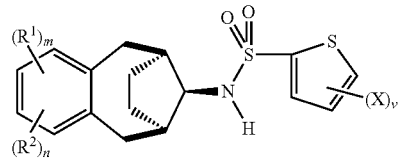

Formula I or pharmaceutically acceptable salts thereof, wherein X, $R^1$, $R^2$, $R^3$, $Z^1$, $Z^2$, m, n, p, q, and v are as defined above for the compounds and pharmaceutically acceptable salts of Formula I.

Formula I above depicts relative stereochemistry, and includes the enantiomers of the following Formulas I' and I", and mixtures of the enantiomers, including a racemic mixture of the enantiomers of Formulas I' and I":

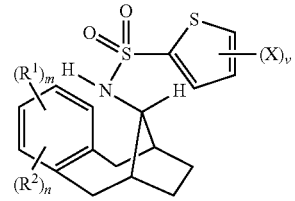

Formula I'

-continued

Formula I″

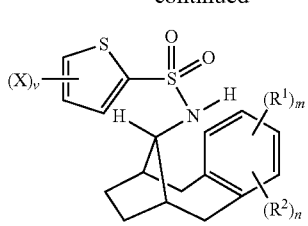

Formula I″ is the corresponding opposite enantiomer of Formula I' when $R^1$, $R^2$, X, m, n, and v of Formula I″ are the same as $R^1$, $R^2$, X, m, n, and v of Formula I' and $R^1$, $R^2$, and X of Formula I″, when present, are in the same positions as $R^1$, $R^2$, and X of Formula I'. Formula I' is the corresponding opposite enantiomer of Formula I″ when $R^1$, $R^2$, X, m, n, and v of Formula I' are the same as $R^1$, $R^2$, X, m, n, and v of Formula I″ and $R^1$, $R^2$, and X of Formula I', when present, are in the same positions as $R^1$, $R^2$, and X of Formula I″.

In some embodiments, the compound of Formula I' is substantially free of its corresponding opposite enantiomer of Formula I″. In other embodiments, the compound of Formula I″ is substantially free of its corresponding opposite enantiomer of Formula I'.

In some embodiments, the compounds of Formula I are those where X is halo. In other embodiments, the compounds of Formula I are those where X is chloro. In other embodiments, the compounds of Formula I are those where v is 1. In other embodiments, v is 1 and X is at the 5-position of the thiopheno group. In other embodiments, v is 1, X is halo, and X is at the 5-position of the thiopheno group. In other embodiments, v is 1, X is chloro, and X is at the 5-position of the thiopheno group.

In some embodiments, the compounds of Formula I are those where $Z^1$ is NH. In some embodiments, the compounds of Formula I are those where $Z^2$, when present, is —$CH_2$—, —$CH_2$—$CH_2$—, —HC=CH—, or —O$CH_2$—$CH_2$—. In other embodiments, the compounds of Formula I are those where $Z^2$ is trans —HC=CH—. In yet other embodiments, the compounds of Formula I are those where $Z^2$ is cis —HC=CH—. In some embodiments, the compounds of Formula I are those where q is 1. In some embodiments, the compounds of Formula I are those where q is 0. In some embodiments, $Z^1$ is NH, q is 1 and $Z^2$ is —$CH_2$—, —$CH_2$—$CH_2$—, —HC=CH—, or —O$CH_2$—$CH_2$—

In some embodiments, the compounds of Formula I are those where each $R^1$ is hydrogen. In some embodiments, the compounds of Formula I are those where p is 1 and $R^3$ is in the 4-position of the phenyl group. In other embodiments, the compounds of Formula I are those where at least one of $R^1$ and $R^3$ is halo or $C_1$-$C_6$ haloalkyl. In certain embodiments, $R^3$ is halo or $C_1$-$C_6$ haloalkyl. In some embodiments, the $C_1$-$C_6$ haloalkyl is trihalomethyl, such as trifluoromethyl, trichloromethyl, tribromomethyl, or triiodomethyl. In some embodiments, halo is fluorine, chlorine, bromine, or iodine. In some embodiments, the compounds of Formula Ia are those where each $R^1$ is hydrogen, p is 1, and $R^3$ is in the 4-position of the phenyl group. In some embodiments, $R^1$ and $R^3$ are $C_1$-$C_6$ haloalkyl, p is 1, and $R^3$ is in the 4-position of the phenyl group. In some embodiments, each $R^1$ is hydrogen, p is 1 or 2 and each $R^3$ is halo or $C_1$-$C_6$ haloalkyl.

In other embodiments, the compounds of Formula I have the following Formula Ia

Formula Ia

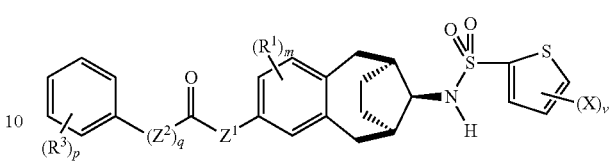

wherein:
X is H, halo, $C_1$-$C_6$ alkyl, $C_1$-$C_6$ haloalkyl, $C_1$-$C_6$ alkoxy, or cyano;
each $R^1$ is independently H, halo, $C_1$-$C_6$ alkyl, $C_1$-$C_6$ haloalkyl, $C_1$-$C_6$ alkoxy, or cyano;
each $R^3$ is independently H, halo, $C_1$-$C_6$ alkyl, $C_1$-$C_6$ haloalkyl, $C_1$-$C_6$ alkoxy, or cyano;
$Z^1$ is NH, O, or $CH_2$;
$Z^2$ is —($C_1$-$C_6$ alkylene)-, —($C_2$-$C_6$ alkenylene)-, or —(O—($C_2$-$C_6$ alkylene))-;
m is 3;
p is an integer from 1 to 5;
q is 0 or 1; and
v is an integer from 1 to 3.

Formula Ia above depicts relative stereochemistry, and includes the enantiomers of the following Formulas Ia' and Ia″, and mixtures of the enantiomers, including a racemic mixture of the enantiomers of Formulas Ia' and Ia″:

Formula Ia'

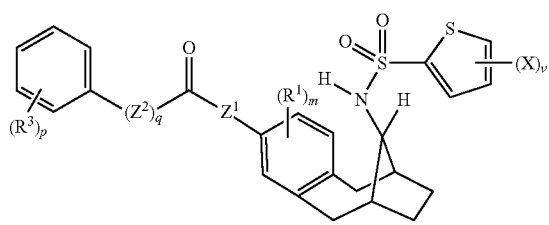

Formula Ia″

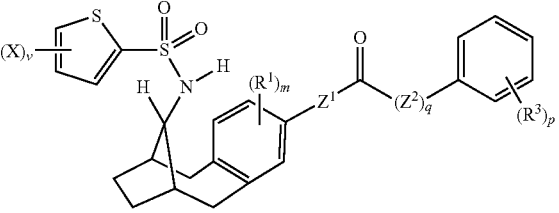

Formula Ia″ is the corresponding opposite enantiomer of Formula Ia' when $R^1$, $R^3$, X, $Z^1$, $Z^2$, q, m, p, and v of Formula Ia″ are the same as $R^1$, $R^3$, X, $Z^1$, $Z^2$, q, m, p, and v of Formula Ia' and $R^1$, $R^3$, and X of Formula Ia″, when present, are in the same positions as $R^1$, $R^3$, and X of Formula Ia'. Formula Ia' is the corresponding opposite enantiomer of Formula Ia″ when $R^1$, $R^3$, X, $Z^1$, $Z^2$, q, m, p, and v of Formula Ia' are the same as $R^1$, $R^3$, X, $Z^1$, $Z^2$, q, m, p, and v of Formula Ia″ and $R^1$, $R^3$, and X of Formula Ia', when present, are in the same positions as $R^1$, $R^3$, and X of Formula Ia″.

In some embodiments, the compound of Formula Ia' is substantially free of its corresponding opposite enantiomer of Formula Ia″. In other embodiments, the compound of Formula Ia″ is substantially free of its corresponding opposite enantiomer of Formula Ia'.

In some embodiments, the compounds of Formula Ia are those where X is halo. In other embodiments, the compounds of Formula Ia are those where X is chloro. In other embodiments, the compounds of Formula Ia are those where v is 1. In other embodiments, v is 1 and X is at the 5-position of the thiopheno group. In other embodiments, v is 1 and X is halo, and X is at the 5-position of the thiopheno group. In other embodiments, v is 1 and X is chloro, and X is at the 5-position of the thiopheno group.

In some embodiments, the compounds of Formula Ia are those where $Z^1$ is NH. In some embodiments, the compounds of Formula Ia are those where $Z^2$, when present, is —$CH_2$—, —$CH_2$—$CH_2$—, —HC=CH—, or —$OCH_2$—$CH_2$—. In other embodiments, the compounds of Formula Ia are those where $Z^2$ is trans —HC=CH—. In yet other embodiments, the compounds of Formula Ia are those where $Z^2$ is cis HC=CH—. In some embodiments, the compounds of Formula Ia are those where q is 1. In some embodiments, the compounds of Formula Ia are those where q is 0. In some embodiments, the compounds of Formula Ia are those where $Z^1$ is NH and $Z^2$ is —$CH_2$—, —$CH_2$—$CH_2$—, —HC=CH—, or —$OCH_2$—$CH_2$—.

In some embodiments, the compounds of Formula Ia are those where each $R^1$ is hydrogen. In some embodiments, the compounds of Formula Ia are those where p is 1 and $R^3$ is in the 4-position of the phenyl group. In other embodiments, the compounds of Formula Ia are those where at least one of $R^1$ and $R^3$ is halo or $C_1$-$C_6$ haloalkyl. In certain embodiments, $R^3$ is halo or $C_1$-$C_6$ haloalkyl. In some embodiments, the $C_1$-$C_6$ haloalkyl is trihalomethyl, such as trifluoromethyl, trichloromethyl, tribromomethyl, or triiodomethyl. In some embodiments, halo is fluorine, chlorine, bromine, or iodine. In some embodiments, the compounds of Formula Ia are those where each $R^1$ is hydrogen, p is 1, and $R^3$ is in the 4-position of the phenyl group. In some embodiments, $R^1$ and $R^3$ are $C_1$-$C_6$ haloalkyl, p is 1, and $R^3$ is in the 4-position of the phenyl group. In some embodiments, each $R^1$ is hydrogen, p is 1 or 2 and each $R^3$ is halo or $C_1$-$C_6$ haloalkyl.

In other embodiments, the compounds of Formula Ia have the following Formula Iaa Formula Iaa

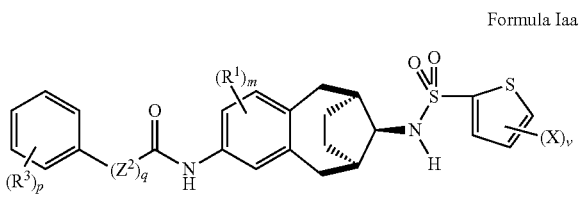

wherein:
X is halo;
each $R^1$ is independently H, halo, $C_1$-$C_6$ alkyl, or $C_1$-$C_6$ haloalkyl;
each $R^3$ is independently H, halo, $C_1$-$C_6$ alkyl, or $C_1$-$C_6$ haloalkyl;
$Z^2$ is —($C_1$-$C_6$ alkylene)-, —($C_2$-$C_6$ alkenylene)-, or —(O—($C_2$-$C_6$ alkylene))-;
m is 3;
p is an integer from 1 to 5;
q is 0 or 1; and
v is an integer from 1 to 3.

Formula Iaa above depicts relative stereochemistry, and includes the enantiomers of the following Formulas Iaa' and Iaa", and mixtures of the enantiomers, including a racemic mixture of the enantiomers of Formulas Iaa' and Iaa":

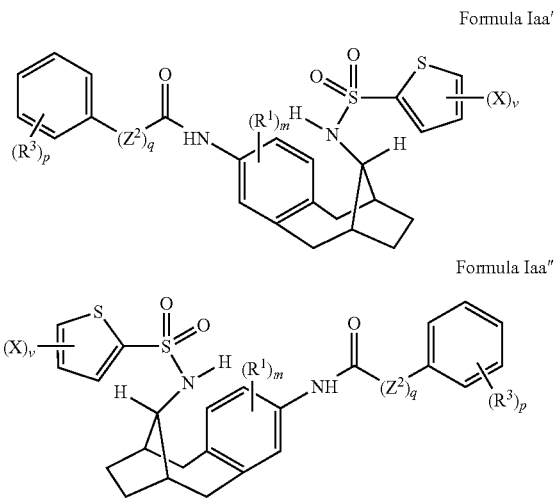

Formula Iaa'

Formula Iaa"

Formula Iaa" is the corresponding opposite enantiomer of Formula Iaa' when $R^1$, $R^3$, X, $Z^2$, q, m, p, and v of Formula Iaa" are the same as $R^1$, $R^3$, X, $Z^2$, q, m, p, and v of Formula Iaa' and $R^1$, $R^3$, and X of Formula Iaa", when present, are in the same positions as $R^1$, $R^3$, and X of Formula Iaa'. Formula Iaa' is the corresponding opposite enantiomer of Formula Iaa" when $R^1$, $R^3$, X, $Z^2$, q, m, p, and v of Formula Iaa' are the same as $R^1$, $R^3$, X, $Z^2$, q, m, p, and v of Formula Iaa" and $R^1$, $R^3$, and X of Formula Iaa', when present, are in the same positions as $R^1$, $R^3$, and X of Formula Iaa".

In some embodiments, the compound of Formula Iaa' is substantially free of its corresponding opposite enantiomer of Formula Iaa". In other embodiments, the compound of Formula Iaa" is substantially free of its corresponding opposite enantiomer of Formula Iaa'.

In some embodiments, the compounds of Formula Iaa are those where X is chloro. In other embodiments, the compounds of Formula Iaa are those where v is 1. In other embodiments, v is 1 and X is at the 5-position of the thiopheno group. In other embodiments, the compounds of Formula Iaa are those where v is 1, X is chloro, and X is at the 5-position of the thiopheno group.

In some embodiments, the compounds of Formula Iaa are those where $R^3$ is halo or (trihalo)methyl. In other embodiments, the compounds of Formula Iaa are those where $R^3$ is fluoro or (trifluoro)methyl. In other embodiments, the compounds of Formula Iaa are those where v is 1, X is chloro, X is at the 5-position of the thiopheno group, and $R^3$ is fluoro or (trifluoro)methyl.

In some embodiments, the compounds of Formula Iaa are those where $Z^2$, when present, is —$CH_2$—, —$CH_2$—$CH_2$—, —HC=CH—, or —$OCH_2$—$CH_2$—. In other embodiments, the compounds of Formula Iaa are those where $Z^2$ is trans —HC=CH—. In yet other embodiments, the compounds of Formula Iaa are those where $Z^2$ is cis —HC=CH—. In some embodiments, the compounds of Formula Iaa are those where q is 1. In some embodiments, the compounds of Formula Iaa are those where q is 0. In some embodiments, the compounds of Formula Iaa are those where q is 1 and $Z^2$ is —$CH_2$—, —$CH_2$—$CH_2$—, —HC=CH—, or —$OCH_2$—$CH_2$—.

In some embodiments, the compounds of Formula Iaa are those where each $R^1$ is hydrogen. In some embodiments, the compounds of Formula Iaa are those where p is 1 and $R^3$ is in the 4-position of the phenyl group. In other embodiments, the compounds of Formula Iaa are those where at least one of $R^1$ and $R^3$ is $C_1$-$C_6$ haloalkyl. In certain embodiments, $R^3$ is $C_1$-$C_6$ haloalkyl. In some embodiments, the $C_1$-$C_6$ haloalkyl is trihalomethyl, such as trifluoromethyl, trichloromethyl, tribromomethyl, or triiodomethyl. In some embodiments, the compounds of Formula Iaa are those where each $R^1$ is hydrogen, p is 1, and $R^3$ is in the 4-position of the phenyl group. In some embodiments, $R^1$ and $R^3$ are each $C_1$-$C_6$ haloalkyl, p is 1, and $R^3$ is in the 4-position of the phenyl group. In some embodiments, each $R^1$ is hydrogen, p is 1 or 2 and each $R^3$ is $C_1$-$C_6$ haloalkyl.

In some embodiments, a compound of Formula Iaa has the structure:

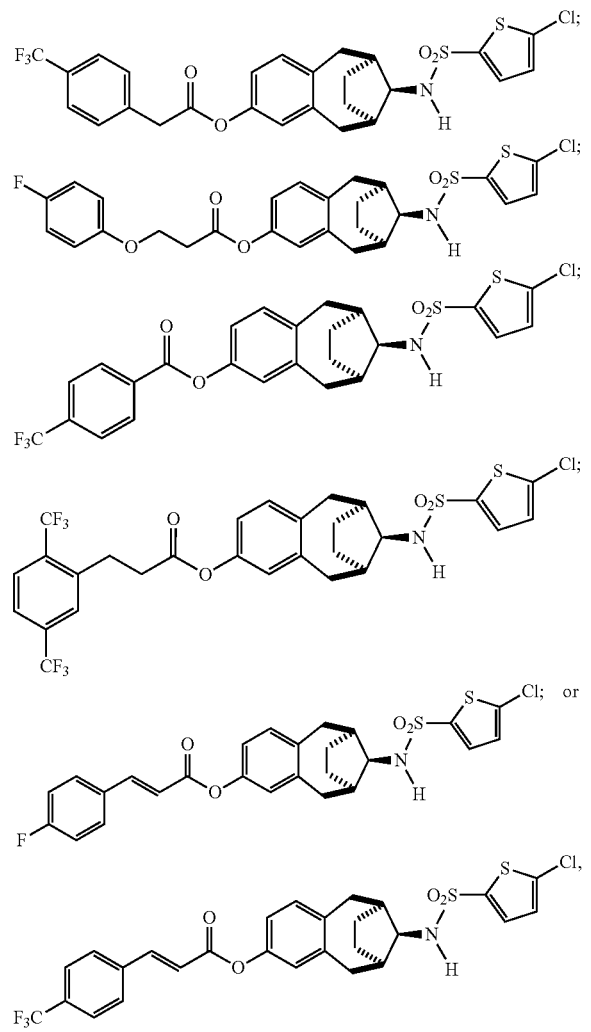

or a pharmaceutically acceptable salt thereof.

In other embodiments, the compounds of Formula Iaa have the Formula Iaaa, set forth below. In some embodiments, the compounds of Formula Iaaa are those where q is 0 or 1. In some embodiments, the compounds of Formula Iaaa are those where $Z^2$, when present, is $CH_2$, $CH_2CH_2$, $O-CH_2CH_2$, or HC=CH. In some embodiments, the compounds of Formula Iaaa are those where Ar is 4-fluorophenyl, 4-bromophenyl, 4-chlorophenyl, 4-iodophenyl, 4-methylphenyl, or 4-(trifluoromethyl)phenyl. In other embodiments, the compounds of Formula Iaaa are those where q is 1, $Z^2$ is $CH_2$, $CH_2CH_2$, $O-CH_2CH_2$, or HC=CH, and Ar is 4-fluorophenyl, 4-bromophenyl, 4-chlorophenyl, 4-iodophenyl, 4-methylphenyl, or 4-(trifluoromethyl)phenyl.

Illustrative examples of the compounds of Formula Iaaa are set forth in Table 1 below.

TABLE 1

Illustrative examples of compounds of Formula Iaaa

Formula Iaaa

| Compound | X | q | $Z^2$ | Ar |
|---|---|---|---|---|
| 1 | Cl | 0 | absent | 4-fluorophenyl |
| 2 | Cl | 0 | absent | 4-chlorophenyl |
| 3 | Cl | 0 | absent | 4-bromophenyl |
| 4 | Cl | 0 | absent | 4-iodophenyl |
| 5 | Cl | 0 | absent | 4-(trifluoromethyl)phenyl |
| 6 | Cl | 0 | absent | 4-methylphenyl |
| 7 | Cl | 1 | $CH_2$ | 4-fluorophenyl |
| 8 | Cl | 1 | $CH_2$ | 4-chlorophenyl |
| 9 | Cl | 1 | $CH_2$ | 4-bromophenyl |
| 10 | Cl | 1 | $CH_2$ | 4-iodophenyl |
| 11 | Cl | 1 | $CH_2$ | 4-(trifluoromethyl)phenyl |
| 12 | Cl | 1 | $CH_2$ | 4-methylphenyl |
| 13 | Cl | 1 | $CH_2CH_2$ | 4-fluorophenyl |
| 14 | Cl | 1 | $CH_2CH_2$ | 4-chlorophenyl |
| 15 | Cl | 1 | $CH_2CH_2$ | 4-bromophenyl |
| 16 | Cl | 1 | $CH_2CH_2$ | 4-iodophenyl |
| 17 | Cl | 1 | $CH_2CH_2$ | 4-(trifluoromethyl)phenyl |
| 18 | Cl | 1 | $CH_2CH_2$ | 4-methylphenyl |
| 19 | Cl | 1 | $CH_2CH_2$ | 2,5-di-(trifluoromethyl)phenyl |
| 20 | Cl | 1 | $CH_2CH_2$ | 2,5-dimethylphenyl |
| 21 | Cl | 1 | $CH_2CH_2$ | 2,5-difluorophenyl |
| 22 | Cl | 1 | $CH_2CH_2$ | 2,5-dichlorophenyl |
| 23 | Cl | 1 | $CH_2CH_2$ | 2,5-dibromophenyl |
| 24 | Cl | 1 | $CH_2CH_2$ | 2,5-diodophenyl |
| 25 | Cl | 1 | $O-CH_2CH_2$ | 4-fluorophenyl |
| 26 | Cl | 1 | $O-CH_2CH_2$ | 4-chlorophenyl |
| 27 | Cl | 1 | $O-CH_2CH_2$ | 4-bromophenyl |
| 28 | Cl | 1 | $O-CH_2CH_2$ | 4-iodophenyl |
| 29 | Cl | 1 | $O-CH_2CH_2$ | 4-(trifluoromethyl)phenyl |
| 30 | Cl | 1 | $O-CH_2CH_2$ | 4-methylphenyl |
| 31 | Cl | 1 | HC=CH | 4-fluorophenyl |
| 32 | Cl | 1 | HC=CH | 4-chlorophenyl |
| 33 | Cl | 1 | HC=CH | 4-bromophenyl |
| 34 | Cl | 1 | HC=CH | 4-iodophenyl |
| 35 | Cl | 1 | HC=CH | 4-(trifluoromethyl)phenyl |
| 36 | Cl | 1 | HC=CH | 4-methylphenyl |
| 37 | F | 0 | absent | 4-fluorophenyl |
| 38 | F | 0 | absent | 4-chlorophenyl |
| 39 | F | 0 | absent | 4-bromophenyl |
| 40 | F | 0 | absent | 4-iodophenyl |
| 41 | F | 0 | absent | 4-(trifluoromethyl)phenyl |
| 42 | F | 0 | absent | 4-methylphenyl |
| 43 | F | 1 | $CH_2$ | 4-fluorophenyl |
| 44 | F | 1 | $CH_2$ | 4-chlorophenyl |
| 45 | F | 1 | $CH_2$ | 4-bromophenyl |
| 46 | F | 1 | $CH_2$ | 4-iodophenyl |
| 47 | F | 1 | $CH_2$ | 4-(trifluoromethyl)phenyl |
| 48 | F | 1 | $CH_2$ | 4-methylphenyl |
| 49 | F | 1 | $CH_2CH_2$ | 4-fluorophenyl |
| 50 | F | 1 | $CH_2CH_2$ | 4-chlorophenyl |
| 51 | F | 1 | $CH_2CH_2$ | 4-bromophenyl |
| 52 | F | 1 | $CH_2CH_2$ | 4-iodophenyl |
| 53 | F | 1 | $CH_2CH_2$ | 4-(trifluoromethyl)phenyl |

TABLE 1-continued

Illustrative examples of compounds of Formula Iaaa

Formula Iaaa

| Compound | X | q | Z² | Ar |
|---|---|---|---|---|
| 54 | F | 1 | CH₂CH₂ | 4-methylphenyl |
| 55 | F | 1 | CH₂CH₂ | 2,5-di-(trifluoromethyl)phenyl |
| 56 | F | 1 | CH₂CH₂ | 2,5-dimethylphenyl |
| 57 | F | 1 | CH₂CH₂ | 2,5-difluorophenyl |
| 58 | F | 1 | CH₂CH₂ | 2,5-dichlorophenyl |
| 59 | F | 1 | CH₂CH₂ | 2,5-dibromophenyl |
| 60 | F | 1 | CH₂CH₂ | 2,5-diiodophenyl |
| 61 | F | 1 | O—CH₂CH₂ | 4-fluorophenyl |
| 62 | F | 1 | O—CH₂CH₂ | 4-chlorophenyl |
| 63 | F | 1 | O—CH₂CH₂ | 4-bromophenyl |
| 64 | F | 1 | O—CH₂CH₂ | 4-iodophenyl |
| 65 | F | 1 | O—CH₂CH₂ | 4-(trifluoromethyl)phenyl |
| 66 | F | 1 | O—CH₂CH₂ | 4-methylphenyl |
| 67 | F | 1 | HC=CH | 4-fluorophenyl |
| 68 | F | 1 | HC=CH | 4-chlorophenyl |
| 69 | F | 1 | HC=CH | 4-bromophenyl |
| 70 | F | 1 | HC=CH | 4-iodophenyl |
| 71 | F | 1 | HC=CH | 4-(trifluoromethyl)phenyl |
| 72 | F | 1 | HC=CH | 4-methylphenyl |
| 73 | Br | 0 | absent | 4-fluorophenyl |
| 74 | Br | 0 | absent | 4-chlorophenyl |
| 75 | Br | 0 | absent | 4-bromophenyl |
| 76 | Br | 0 | absent | 4-iodophenyl |
| 77 | Br | 0 | absent | 4-(trifluoromethyl)phenyl |
| 78 | Br | 0 | absent | 4-methylphenyl |
| 79 | Br | 1 | CH₂ | 4-fluorophenyl |
| 80 | Br | 1 | CH₂ | 4-chlorophenyl |
| 81 | Br | 1 | CH₂ | 4-bromophenyl |
| 82 | Br | 1 | CH₂ | 4-iodophenyl |
| 83 | Br | 1 | CH₂ | 4-(trifluoromethyl)phenyl |
| 84 | Br | 1 | CH₂ | 4-methylphenyl |
| 85 | Br | 1 | CH₂CH₂ | 4-fluorophenyl |
| 86 | Br | 1 | CH₂CH₂ | 4-chlorophenyl |
| 87 | Br | 1 | CH₂CH₂ | 4-bromophenyl |
| 88 | Br | 1 | CH₂CH₂ | 4-iodophenyl |
| 89 | Br | 1 | CH₂CH₂ | 4-(trifluoromethyl)phenyl |
| 90 | Br | 1 | CH₂CH₂ | 4-methylphenyl |
| 91 | Br | 1 | CH₂CH₂ | 2,5-di-(trifluoromethyl)phenyl |
| 92 | Br | 1 | CH₂CH₂ | 2,5-dimethylphenyl |
| 93 | Br | 1 | CH₂CH₂ | 2,5-difluorophenyl |
| 94 | Br | 1 | CH₂CH₂ | 2,5-dichlorophenyl |
| 95 | Br | 1 | CH₂CH₂ | 2,5-dibromophenyl |
| 96 | Br | 1 | CH₂CH₂ | 2,5-diiodophenyl |
| 97 | Br | 1 | O—CH₂CH₂ | 4-fluorophenyl |
| 98 | Br | 1 | O—CH₂CH₂ | 4-chlorophenyl |
| 99 | Br | 1 | O—CH₂CH₂ | 4-bromophenyl |
| 100 | Br | 1 | O—CH₂CH₂ | 4-iodophenyl |
| 101 | Br | 1 | O—CH₂CH₂ | 4-(trifluoromethyl)phenyl |
| 102 | Br | 1 | O—CH₂CH₂ | 4-methylphenyl |
| 103 | Br | 1 | HC=CH | 4-fluorophenyl |
| 104 | Br | 1 | HC=CH | 4-chlorophenyl |
| 105 | Br | 1 | HC=CH | 4-bromophenyl |
| 106 | Br | 1 | HC=CH | 4-iodophenyl |
| 107 | Br | 1 | HC=CH | 4-(trifluoromethyl)phenyl |
| 108 | Br | 1 | HC=CH | 4-methylphenyl |
| 109 | I | 0 | absent | 4-fluorophenyl |
| 110 | I | 0 | absent | 4-chlorophenyl |
| 111 | I | 0 | absent | 4-bromophenyl |
| 112 | I | 0 | absent | 4-iodophenyl |
| 113 | I | 0 | absent | 4-(trifluoromethyl)phenyl |
| 114 | I | 0 | absent | 4-methylphenyl |
| 115 | I | 1 | CH₂ | 4-fluorophenyl |
| 116 | I | 1 | CH₂ | 4-chlorophenyl |
| 117 | I | 1 | CH₂ | 4-bromophenyl |
| 118 | I | 1 | CH₂ | 4-iodophenyl |
| 119 | I | 1 | CH₂ | 4-(trifluoromethyl)phenyl |
| 120 | I | 1 | CH₂ | 4-methylphenyl |
| 121 | I | 1 | CH₂CH₂ | 4-fluorophenyl |
| 122 | I | 1 | CH₂CH₂ | 4-chlorophenyl |
| 123 | I | 1 | CH₂CH₂ | 4-bromophenyl |
| 124 | I | 1 | CH₂CH₂ | 4-iodophenyl |
| 125 | I | 1 | CH₂CH₂ | 4-(trifluoromethyl)phenyl |
| 126 | I | 1 | CH₂CH₂ | 4-methylphenyl |
| 127 | I | 1 | CH₂CH₂ | 2,5-di-(trifluoromethyl)phenyl |
| 128 | I | 1 | CH₂CH₂ | 2,5-dimethylphenyl |
| 129 | I | 1 | CH₂CH₂ | 2,5-difluorophenyl |
| 130 | I | 1 | CH₂CH₂ | 2,5-dichlorophenyl |
| 131 | I | 1 | CH₂CH₂ | 2,5-dibromophenyl |
| 132 | I | 1 | CH₂CH₂ | 2,5-diiodophenyl |
| 133 | I | 1 | O—CH₂CH₂ | 4-fluorophenyl |
| 134 | I | 1 | O—CH₂CH₂ | 4-chlorophenyl |
| 135 | I | 1 | O—CH₂CH₂ | 4-bromophenyl |
| 136 | I | 1 | O—CH₂CH₂ | 4-iodophenyl |
| 137 | I | 1 | O—CH₂CH₂ | 4-(trifluoromethyl)phenyl |
| 138 | I | 1 | O—CH₂CH₂ | 4-methylphenyl |
| 139 | I | 1 | HC=CH | 4-fluorophenyl |
| 140 | I | 1 | HC=CH | 4-chlorophenyl |
| 141 | I | 1 | HC=CH | 4-bromophenyl |
| 142 | I | 1 | HC=CH | 4-iodophenyl |
| 143 | I | 1 | HC=CH | 4-(trifluoromethyl)phenyl |
| 144 | I | 1 | HC=CH | 4-methylphenyl | and the enantiomer having the Formula Iaaa', the enantiomer having the Formula Iaaa'', and mixtures thereof, of each of Compounds 1-144, and pharmaceutically acceptable salts thereof The structures of Formulas Iaaa' and Iaaa'' are depicted below:

Formula Iaaa'

-continued

Formula Iaaa"

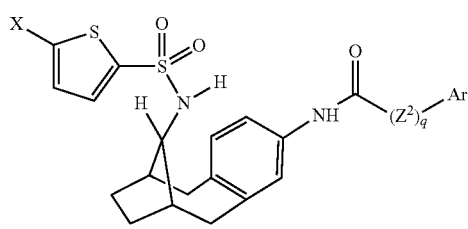

Formula Iaaa" is the corresponding opposite enantiomer of Formula Iaaa' when Ar, X, $Z^2$, and q of Formula Iaaa" are the same as Ar, X, $Z^2$, and q of Formula Iaaa'. Formula Iaaa' is the corresponding opposite enantiomer of Formula Iaaa" when Ar, X, $Z^2$, and q of Formula Iaaa' are the same as Ar, X, $Z^2$, and q of Formula Iaaa".

In one embodiment, $Z^2$ of Compound 31-36, 67-72, 103-108, or 139-144 is cis. In another embodiment, $Z^2$ of Compound 31-36, 67-72, 103-108, or 139-144 is trans.

In another embodiment, the Sulfonamide-Based Compounds are compounds of the following Formula II Formula II

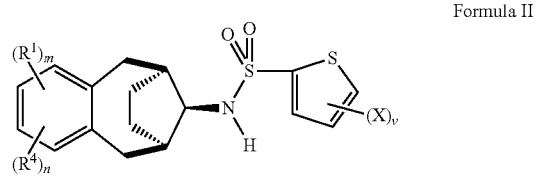

or pharmaceutically acceptable salts thereof, wherein X, $R^1$, $R^3$, $R^4$, $R^5$, $Z^1$, $Z^2$, m, n, p, t, q, and v are as defined above for the compounds and pharmaceutically acceptable salts of Formula II.

Formula II above depicts relative stereochemistry, and includes the enantiomers of the following Formulas II' and II", and mixtures of the enantiomers, including a racemic mixture of the enantiomers of Formulas II' and II":

Formula II'

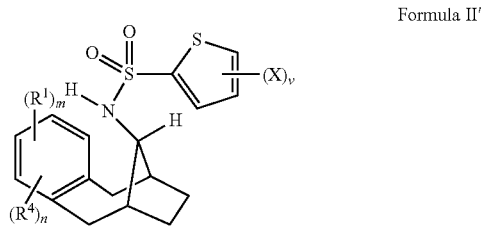

Formula II"

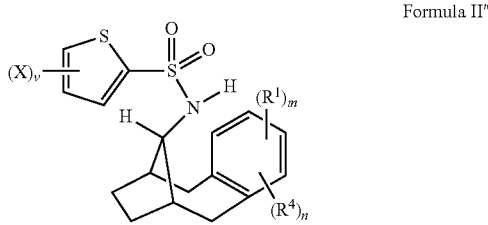

Formula II" is the corresponding opposite enantiomer of Formula II' when $R^1$, $R^4$, X, m, n, and v of Formula II" are the same as $R^1$, $R^4$, X, m, n, and v of Formula II' and $R^1$, $R^4$, and X of Formula II", when present, are in the same positions as $R^1$, $R^4$, and X of Formula I'. Formula II' is the corresponding opposite enantiomer of Formula II" when $R^1$, $R^4$, X, m, n, and v of Formula II' are the same as $R^1$, $R^4$, X, m, n, and v of Formula II" and $R^1$, $R^4$, and X of Formula II', when present, are in the same positions as $R^1$, $R^4$, and X of Formula II".

In some embodiments, the compound of Formula II' is substantially free of its corresponding opposite enantiomer of Formula II". In other embodiments, the compound of Formula II" is substantially free of its corresponding opposite enantiomer of Formula II'.

In some embodiments, the compounds of Formula II are those where X is halo. In other embodiments, the compounds of Formula II are those where X is chloro. In other embodiments, the compounds of Formula II are those where v is 1. In other embodiments, v is 1 and X is at the 5-position of the thiopheno group. In other embodiments, v is 1, X is halo, and X is at the 5-position of the thiopheno group. In other embodiments, v is 1, X is chloro, and X is at the 5-position of the thiopheno group.

In some embodiments, the compounds of Formula II are those where $Z^1$ is NH. In some embodiments, the compounds of Formula II are those where $Z^2$, when present, is —$CH_2$—$CH_2$—, or —HC=CH—. In other embodiments, the compounds of Formula II are those where $Z^2$ is trans —HC=CH—. In yet other embodiments, the compounds of Formula II are those where $Z^2$ is cis —HC=CH—. In some embodiments, the compounds of Formula II are those where q is 1. In some embodiments, the compounds of Formula II are those where q is 0. In some embodiments, $Z^1$ is NH, q is 1 and $Z^2$ is —$CH_2$—$CH_2$—, —HC=CH—, or —$OCH_2$—$CH_2$—.

In some embodiments, the compounds of Formula II are those where each $R^1$ is hydrogen. In other embodiments, the compounds of Formula II are those where at least one of $R^1$ and $R^3$ is $C_1$-$C_6$ haloalkyl. In some embodiments, the $C_1$-$C_6$ haloalkyl is trihalomethyl, such as trifluoromethyl, trichloromethyl, tribromomethyl, or triiodomethyl.

In other embodiments, the compounds of Formula II are those where $R^5$ is hydrogen or methyl. In other embodiments, the compounds of Formula II are those where $R^5$ is methyl. In other embodiments, the compounds of Formula II are those where each $R^1$ is hydrogen and $R^5$ is hydrogen or methyl. In other embodiments, the compounds of Formula II are those where $R^1$ and $R^3$ are $C_1$-$C_6$ haloalkyl and $R^5$ is hydrogen or methyl.

In other embodiments, the compounds of Formula II have the following Formula IIa Formula IIa

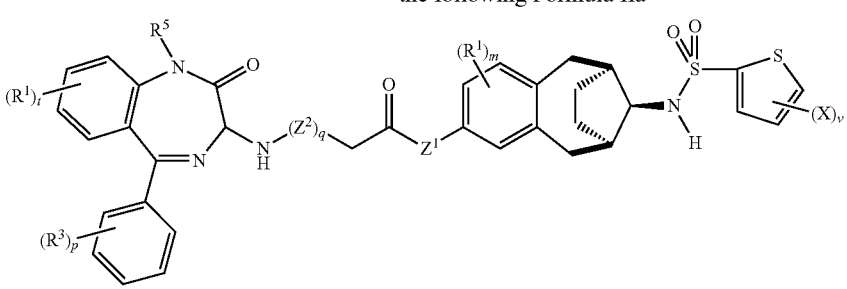

wherein:

X is H, halo, $C_1$-$C_6$ alkyl, $C_1$-$C_6$ haloalkyl, $C_1$-$C_6$ alkoxy, or cyano;

each $R^1$ is independently H, halo, $C_1$-$C_6$ alkyl, $C_1$-$C_6$ haloalkyl, $C_1$-$C_6$ alkoxy, or cyano;

each $R^3$ is independently H, halo, $C_1$-$C_6$ alkyl, $C_1$-$C_6$ haloalkyl, $C_1$-$C_6$ alkoxy, or cyano;

$R^5$ is H, $C_1$-$C_6$ alkyl, or $C_1$-$C_6$ haloalkyl;

$Z^1$ is NH, O or $CH_2$;

$Z^2$ is —($C_1$-$C_6$ alkylene)- or —($C_2$-$C_6$ alkenylene)-;

m is 3;

p is 5;

t is 4;

q is 0 or 1; and v is an integer from 1 to 3.

Formula IIa above depicts relative stereochemistry, and includes the enantiomers of the following Formulas IIa' and IIa", and mixtures of the enantiomers, including a racemic mixture of the enantiomers of Formulas IIa' and IIa":

of Formula IIa are those where X is chloro. In other embodiments, the compounds of Formula IIa are those where v is 1. In other embodiments, v is 1 and X is at the 5-position of the thiopheno group. In other embodiments, v is 1, X is halo, and X is at the 5-position of the thiopheno group. In other embodiments, v is 1, X is chloro, and X is at the 5-position of the thiopheno group.

In some embodiments, the compounds of Formula IIa are those where $Z^1$ is NH. In some embodiments, the compounds of Formula IIa are those where $Z^2$, when present, is —$CH_2$—$CH_2$—, or —HC=CH—. In other embodiments, the compounds of Formula IIa are those where $Z^2$ is trans —HC=CH—. In yet other embodiments, the compounds of Formula IIa are those where $Z^2$ is cis —HC=CH—. In some embodiments, the compounds of Formula IIa are those where q is 1. In some embodiments, the compounds of Formula IIa are those where q is 0. In some embodiments, $Z^1$ is NH, q is 1 and $Z^2$ is —$CH_2$—$CH_2$—, —HC=CH—, or —$OCH_2$—$CH_2$—.

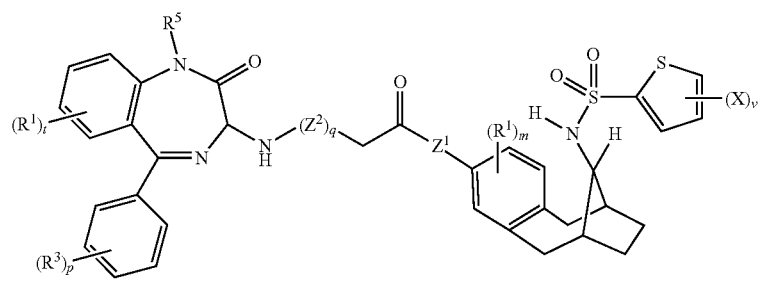

Formula IIa'

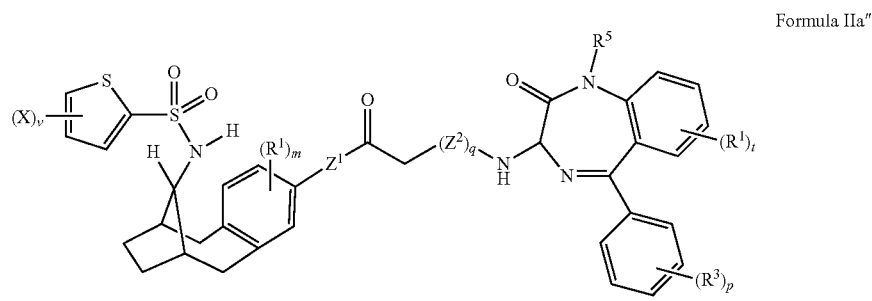

Formula IIa"

Formula IIa" is the corresponding opposite enantiomer of Formula IIa' when $R^1$, $R^3$, $R^5$, X, $Z^1$, $Z^2$, q, m, p, t, and v of Formula IIa" are the same as $R^1$, $R^3$, $R^5$, X, $Z^1$, $Z^2$, q, m, p, t, and v of Formula IIa' and $R^1$, $R^3$, and X of Formula IIa", when present, are in the same positions as $R^1$, $R^3$, and X of Formula IIa'. Formula IIa' is the corresponding opposite enantiomer of Formula IIa" when $R^1$, $R^3$, $R^5$, X, $Z^1$, $Z^2$, q, m, p, t, and v of Formula IIa' are the same as $R^1$, $R^3$, $R^5$, X, $Z^1$, $Z^2$, q, m, p, t, and v of Formula IIa" and $R^1$, $R^3$, and X of Formula IIa', when present, are in the same positions as $R^1$, $R^3$, and X of Formula IIa".

In some embodiments, the compound of Formula IIa' is substantially free of its corresponding opposite enantiomer of Formula IIa". In other embodiments, the compound of Formula IIa" is substantially free of its corresponding opposite enantiomer of Formula IIa'.

In some embodiments, the compounds of Formula IIa are those where X is halo. In other embodiments, the compounds In some embodiments, the compounds of Formula IIa are those where each $R^1$ is hydrogen. In other embodiments, the compounds of Formula IIa are those where at least one of $R^1$ and $R^3$ is $C_1$-$C_6$ haloalkyl. In certain embodiments, $R^3$ is $C_1$-$C_6$ haloalkyl. In some embodiments, the $C_1$-$C_6$ haloalkyl is trihalomethyl, such as trifluoromethyl, trichloromethyl, tribromomethyl, or triiodomethyl.

In other embodiments, the compounds of Formula IIa are those where $R^5$ is hydrogen or methyl. In other embodiments, the compounds of Formula IIa are those where $R^5$ is methyl. In other embodiments, the compounds of Formula II are those where each $R^1$ is hydrogen and $R^5$ is hydrogen or methyl. In other embodiments, the compounds of Formula II are those where $R^1$ and $R^3$ are $C_1$-$C_6$ haloalkyl and $R^5$ is hydrogen or methyl.

In other embodiments, the compounds of Formula IIa have the following Formula IIaa

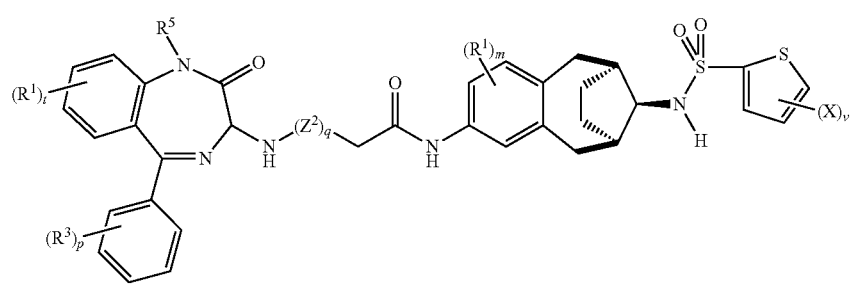

Formula IIaa wherein:
X is halo;
each $R^1$ is independently H, halo, $C_1$-$C_6$ alkyl, or $C_1$-$C_6$ haloalkyl;
each $R^3$ is independently H, halo, $C_1$-$C_6$ alkyl, or $C_1$-$C_6$ haloalkyl;
$Z^2$ is —($C_1$-$C_6$ alkylene)- or —($C_2$-$C_6$ alkenylene)-;
$R^5$ is H, $C_1$-$C_6$ alkyl, or $C_1$-$C_6$ haloalkyl;
m is 3;
p is 5;
t is 4;
q is 0 or 1; and
v is an integer from 1 to 3.

Formula IIaa above depicts relative stereochemistry, and includes the enantiomers of the following Formulas IIaa' and IIaa", and mixtures of the enantiomers, including a racemic mixture of the enantiomers of Formulas IIaa' and IIaa":

v of Formula IIaa' and $R^1$, $R^3$, and X of Formula IIaa", when present, are in the same positions as $R^1$, $R^3$, and X of Formula IIaa'. Formula IIaa' is the corresponding opposite enantiomer of Formula Iaa" when $R^1$, $R^3$, $R^5$, X, $Z^2$, q, m, p, t, and v of Formula IIaa' are the same as $R^1$, $R^3$, $R^5$, X, $Z^2$, q, m, p, t, and v of Formula IIaa" and $R^1$, $R^3$, and X of Formula IIaa', when present, are in the same positions as $R^1$, $R^3$, and X of Formula IIaa".

In some embodiments, the compound of Formula IIaa' is substantially free of its corresponding opposite enantiomer of Formula IIaa". In other embodiments, the compound of Formula IIaa" is substantially free of its corresponding opposite enantiomer of Formula IIaa'.

In some embodiments, the compounds of Formula IIaa are those where X is chloro. In other embodiments of the compound of Formula IIaa, v is 1. In other embodiments, v is 1 and X is at the 5-position of the thiopheno group. In other embodiments, v is 1, X is chloro, and X is at the 5-position of the thiopheno group.

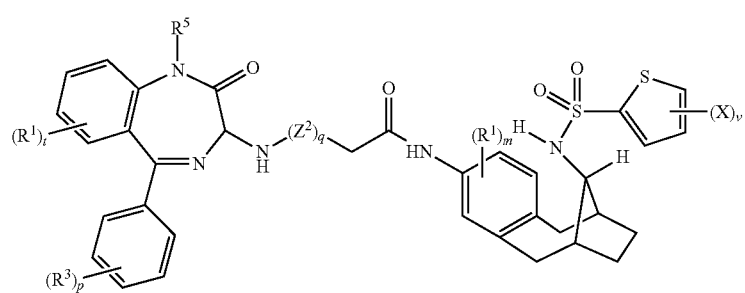

Formula IIaa'

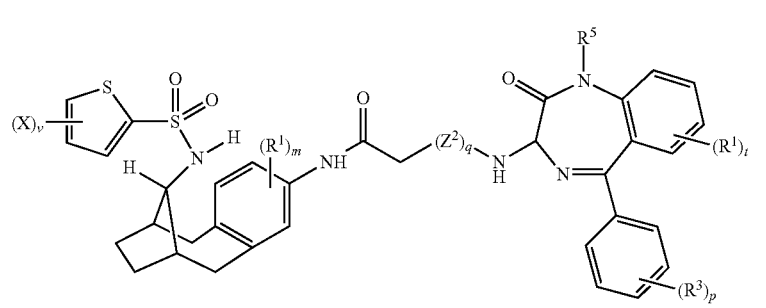

Formula IIaa"

Formula IIaa" is the corresponding opposite enantiomer of Formula IIaa' when $R^1$, $R^3$, $R^5$, X, $Z^2$, q, m, p, t, and v of Formula IIaa" are the same as $R^1$, $R^3$, $R^5$, X, $Z^2$, q, m, p, t, and In some embodiments, the compounds of Formula IIaa are those where $Z^2$, when present, is —$CH_2$—, —$CH_2$—$CH_2$—, or —HC=CH—. In other embodiments, the compounds of Formula IIaa are those where $Z^2$ is trans —HC=CH—. In yet other embodiments, the compounds of Formula IIaa are those where $Z^2$ is cis —HC=CH—. In some embodiments, the compounds of Formula IIaa are those where q is 1. In some embodiments, the compounds of Formula IIaa are those where q is 0. In some embodiments, $Z^1$ is NH, q is 1 and $Z^2$ is —CH$_2$—, —CH$_2$—CH$_2$—, —HC=CH—, or —OCH$_2$—CH$_2$—.

In some embodiments, the compounds of Formula IIaa are those where each $R^1$ is hydrogen. In other embodiments, the compounds of Formula IIaa are those where at least one of $R^1$ and $R^3$ is halo or $C_1$-$C_6$ haloalkyl. In certain embodiments, $R^3$ is halo or $C_1$-$C_6$ haloalkyl. In some embodiments, the $C_1$-$C_6$ haloalkyl is trihalomethyl, such as trifluoromethyl, trichloromethyl, tribromomethyl, or triiodomethyl. In some embodiments, halo is fluorine, chlorine, bromine, or iodine.

In other embodiments, the compounds of Formula IIaa are those where $R^5$ is hydrogen or methyl. In other embodiments, the compounds of Formula IIaa are those where $R^5$ is methyl. In other embodiments, the compounds of Formula II are those where each $R^1$ is hydrogen and $R^5$ is hydrogen or methyl. In other embodiments, the compounds of Formula II are those where $R^1$ and $R^3$ are $C_1$-$C_6$ haloalkyl and $R^5$ is hydrogen or methyl.

In some embodiments, a compound of Formula IIaa has the structure:

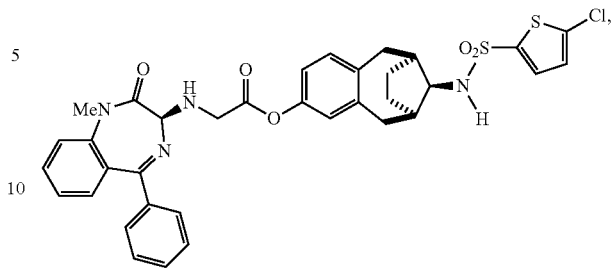

or a pharmaceutically acceptable salt thereof.

In other embodiments, the compounds of Formula IIaa have the Formula IIaaa, set forth below. In some embodiments, the compounds of Formula IIaaa are those where q is 0 or 1. In some embodiments, the compounds of Formula IIaaa are those where $Z^2$ is CH$_2$. In some embodiments, the compounds of Formula IIaaa are those where $R^5$ is H or CH$_3$. In some embodiments, the compounds of Formula IIaaa are those where $R^{3a}$, $R^{3b}$, and $R^{3c}$ are independently H, fluoro, CH$_3$, or CF$_3$. In some embodiments, the compounds of Formula IIaaa are those where q is 1, $Z^2$ is CH$_2$, $R^5$ is H or CH$_3$, and $R^{3a}$, $R^{3b}$, and $R^{3c}$ are independently H, fluoro, CH$_3$, or CF$_3$.

Illustrative examples of the compounds of Formula IIaaa are set forth in Table 2 below.

TABLE 2

Illustrative examples of compounds of Formula IIaaa

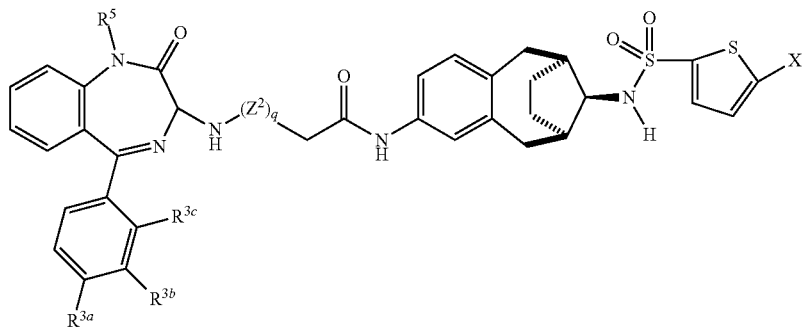

| Compound | X | $R^5$ | q | $Z^2$ | $R^{3a}$ | $R^{3b}$ | $R^{3c}$ |
|---|---|---|---|---|---|---|---|
| 145 | Cl | H | 0 | absent | H | H | H |
| 146 | Cl | H | 0 | absent | F | H | H |
| 147 | Cl | H | 0 | absent | H | F | H |
| 148 | Cl | H | 0 | absent | H | H | F |
| 149 | Cl | H | 0 | absent | CH$_3$ | H | H |
| 150 | Cl | H | 0 | absent | H | CH$_3$ | H |
| 151 | Cl | H | 0 | absent | H | H | CH$_3$ |
| 152 | Cl | H | 0 | absent | CF$_3$ | H | H |
| 153 | Cl | H | 0 | absent | H | CF$_3$ | H |
| 154 | Cl | H | 0 | absent | H | H | CF$_3$ |
| 155 | Cl | H | 1 | CH$_2$ | H | H | H |
| 156 | Cl | H | 1 | CH$_2$ | F | H | H |
| 157 | Cl | H | 1 | CH$_2$ | H | F | H |
| 158 | Cl | H | 1 | CH$_2$ | H | H | F |
| 159 | Cl | H | 1 | CH$_2$ | CH$_3$ | H | H |
| 160 | Cl | H | 1 | CH$_2$ | H | CH$_3$ | H |
| 161 | Cl | H | 1 | CH$_2$ | H | H | CH$_3$ |
| 162 | Cl | H | 1 | CH$_2$ | CF$_3$ | H | H |
| 163 | Cl | H | 1 | CH$_2$ | H | CF$_3$ | H |
| 164 | Cl | H | 1 | CH$_2$ | H | H | CF$_3$ |
| 165 | Cl | CH$_3$ | 0 | absent | H | H | H |
| 166 | Cl | CH$_3$ | 0 | absent | F | H | H |

TABLE 2-continued

Illustrative examples of compounds of Formula IIaaa

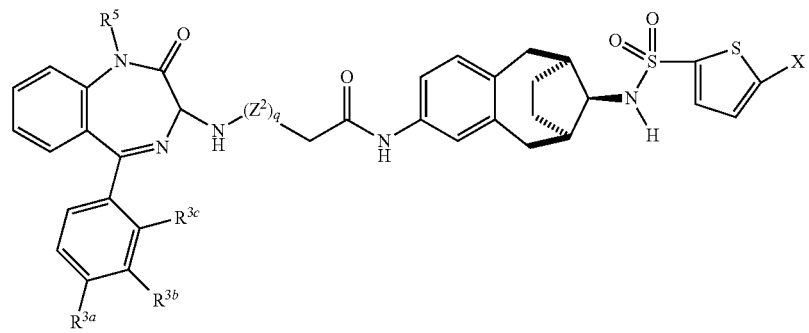

| Compound | X | R⁵ | q | Z² | R³ᵃ | R³ᵇ | R³ᶜ |
|---|---|---|---|---|---|---|---|
| 167 | Cl | CH₃ | 0 | absent | H | F | H |
| 168 | Cl | CH₃ | 0 | absent | H | H | F |
| 169 | Cl | CH₃ | 0 | absent | CH₃ | H | H |
| 170 | Cl | CH₃ | 0 | absent | H | CH₃ | H |
| 171 | Cl | CH₃ | 0 | absent | H | H | CH₃ |
| 172 | Cl | CH₃ | 0 | absent | CF₃ | H | H |
| 173 | Cl | CH₃ | 0 | absent | H | CF₃ | H |
| 174 | Cl | CH₃ | 0 | absent | H | H | CF₃ |
| 175 | Cl | CH₃ | 1 | CH₂ | H | H | H |
| 176 | Cl | CH₃ | 1 | CH₂ | F | H | H |
| 177 | Cl | CH₃ | 1 | CH₂ | H | F | H |
| 178 | Cl | CH₃ | 1 | CH₂ | H | H | F |
| 179 | Cl | CH₃ | 1 | CH₂ | CH₃ | H | H |
| 180 | Cl | CH₃ | 1 | CH₂ | H | CH₃ | H |
| 181 | Cl | CH₃ | 1 | CH₂ | H | H | CH₃ |
| 182 | Cl | CH₃ | 1 | CH₂ | CF₃ | H | H |
| 183 | Cl | CH₃ | 1 | CH₂ | H | CF₃ | H |
| 184 | Cl | CH₃ | 1 | CH₂ | H | H | CF₃ |
| 185 | F | H | 0 | absent | H | H | H |
| 186 | F | H | 0 | absent | F | H | H |
| 187 | F | H | 0 | absent | H | F | H |
| 188 | F | H | 0 | absent | H | H | F |
| 189 | F | H | 0 | absent | CH₃ | H | H |
| 190 | F | H | 0 | absent | H | CH₃ | H |
| 191 | F | H | 0 | absent | H | H | CH₃ |
| 192 | F | H | 0 | absent | CF₃ | H | H |
| 193 | F | H | 0 | absent | H | CF₃ | H |
| 194 | F | H | 0 | absent | H | H | CF₃ |
| 195 | F | H | 1 | CH₂ | H | H | H |
| 196 | F | H | 1 | CH₂ | F | H | H |
| 197 | F | H | 1 | CH₂ | H | F | H |
| 198 | F | H | 1 | CH₂ | H | H | F |
| 199 | F | H | 1 | CH₂ | CH₃ | H | H |
| 200 | F | H | 1 | CH₂ | H | CH₃ | H |
| 201 | F | H | 1 | CH₂ | H | H | CH₃ |
| 202 | F | H | 1 | CH₂ | CF₃ | H | H |
| 203 | F | H | 1 | CH₂ | H | CF₃ | H |
| 204 | F | H | 1 | CH₂ | H | H | CF₃ |
| 205 | F | CH₃ | 0 | absent | H | H | H |
| 206 | F | CH₃ | 0 | absent | F | H | H |
| 207 | F | CH₃ | 0 | absent | H | F | H |
| 208 | F | CH₃ | 0 | absent | H | H | F |
| 209 | F | CH₃ | 0 | absent | CH₃ | H | H |
| 210 | F | CH₃ | 0 | absent | H | CH₃ | H |
| 211 | F | CH₃ | 0 | absent | H | H | CH₃ |
| 212 | F | CH₃ | 0 | absent | CF₃ | H | H |
| 213 | F | CH₃ | 0 | absent | H | CF₃ | H |
| 214 | F | CH₃ | 0 | absent | H | H | CF₃ |
| 215 | F | CH₃ | 1 | CH₂ | H | H | H |
| 216 | F | CH₃ | 1 | CH₂ | F | H | H |
| 217 | F | CH₃ | 1 | CH₂ | H | F | H |
| 218 | F | CH₃ | 1 | CH₂ | H | H | F |
| 219 | F | CH₃ | 1 | CH₂ | CH₃ | H | H |
| 220 | F | CH₃ | 1 | CH₂ | H | CH₃ | H |
| 221 | F | CH₃ | 1 | CH₂ | H | H | CH₃ |
| 222 | F | CH₃ | 1 | CH₂ | CF₃ | H | H |
| 223 | F | CH₃ | 1 | CH₂ | H | CF₃ | H |
| 224 | F | CH₃ | 1 | CH₂ | H | H | CF₃ |
| 225 | Br | H | 0 | absent | H | H | H |

TABLE 2-continued

Illustrative examples of compounds of Formula IIaaa

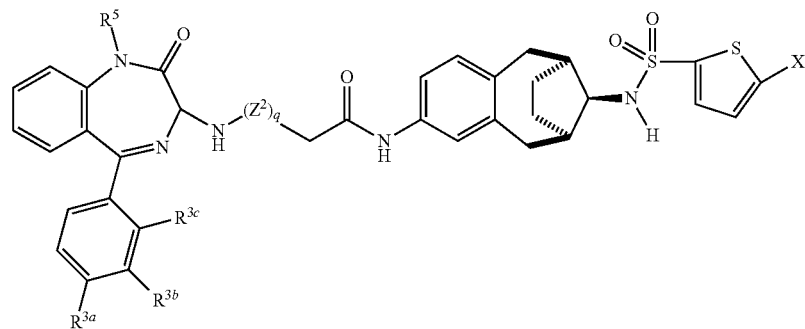

| Compound | X | R⁵ | q | Z² | R³ᵃ | R³ᵇ | R³ᶜ |
|---|---|---|---|---|---|---|---|
| 226 | Br | H | 0 | absent | F | H | H |
| 227 | Br | H | 0 | absent | H | F | H |
| 228 | Br | H | 0 | absent | H | H | F |
| 229 | Br | H | 0 | absent | CH₃ | H | H |
| 230 | Br | H | 0 | absent | H | CH₃ | H |
| 231 | Br | H | 0 | absent | H | H | CH₃ |
| 232 | Br | H | 0 | absent | CF₃ | H | H |
| 233 | Br | H | 0 | absent | H | CF₃ | H |
| 234 | Br | H | 0 | absent | H | H | CF₃ |
| 235 | Br | H | 1 | CH₂ | H | H | H |
| 236 | Br | H | 1 | CH₂ | F | H | H |
| 237 | Br | H | 1 | CH₂ | H | F | H |
| 238 | Br | H | 1 | CH₂ | H | H | F |
| 239 | Br | H | 1 | CH₂ | CH₃ | H | H |
| 240 | Br | H | 1 | CH₂ | H | CH₃ | H |
| 241 | Br | H | 1 | CH₂ | H | H | CH₃ |
| 242 | Br | H | 1 | CH₂ | CF₃ | H | H |
| 243 | Br | H | 1 | CH₂ | H | CF₃ | H |
| 244 | Br | H | 1 | CH₂ | H | H | CF₃ |
| 245 | Br | CH₃ | 0 | absent | H | H | H |
| 246 | Br | CH₃ | 0 | absent | F | H | H |
| 247 | Br | CH₃ | 0 | absent | H | F | H |
| 248 | Br | CH₃ | 0 | absent | H | H | F |
| 249 | Br | CH₃ | 0 | absent | CH₃ | H | H |
| 250 | Br | CH₃ | 0 | absent | H | CH₃ | H |
| 251 | Br | CH₃ | 0 | absent | H | H | CH₃ |
| 252 | Br | CH₃ | 0 | absent | CF₃ | H | H |
| 253 | Br | CH₃ | 0 | absent | H | CF₃ | H |
| 254 | Br | CH₃ | 0 | absent | H | H | CF₃ |
| 255 | Br | CH₃ | 1 | CH₂ | H | H | H |
| 256 | Br | CH₃ | 1 | CH₂ | F | H | H |
| 257 | Br | CH₃ | 1 | CH₂ | H | F | H |
| 258 | Br | CH₃ | 1 | CH₂ | H | H | F |
| 259 | Br | CH₃ | 1 | CH₂ | CH₃ | H | H |
| 260 | Br | CH₃ | 1 | CH₂ | H | CH₃ | H |
| 261 | Br | CH₃ | 1 | CH₂ | H | H | CH₃ |
| 262 | Br | CH₃ | 1 | CH₂ | CF₃ | H | H |
| 263 | Br | CH₃ | 1 | CH₂ | H | CF₃ | H |
| 264 | Br | CH₃ | 1 | CH₂ | H | H | CF₃ |
| 265 | I | H | 0 | absent | H | H | H |
| 266 | I | H | 0 | absent | F | H | H |
| 267 | I | H | 0 | absent | H | F | H |
| 268 | I | H | 0 | absent | H | H | F |
| 269 | I | H | 0 | absent | CH₃ | H | H |
| 270 | I | H | 0 | absent | H | CH₃ | H |
| 271 | I | H | 0 | absent | H | H | CH₃ |
| 272 | I | H | 0 | absent | CF₃ | H | H |
| 273 | I | H | 0 | absent | H | CF₃ | H |
| 274 | I | H | 0 | absent | H | H | CF₃ |
| 275 | I | H | 1 | CH₂ | H | H | H |
| 276 | I | H | 1 | CH₂ | F | H | H |
| 277 | I | H | 1 | CH₂ | H | F | H |
| 278 | I | H | 1 | CH₂ | H | H | F |
| 279 | I | H | 1 | CH₂ | CH₃ | H | H |
| 280 | I | H | 1 | CH₂ | H | CH₃ | H |
| 281 | I | H | 1 | CH₂ | H | H | CH₃ |
| 282 | I | H | 1 | CH₂ | CF₃ | H | H |
| 283 | I | H | 1 | CH₂ | H | CF₃ | H |
| 284 | I | H | 1 | CH₂ | H | H | CF₃ |

TABLE 2-continued

Illustrative examples of compounds of Formula IIaaa

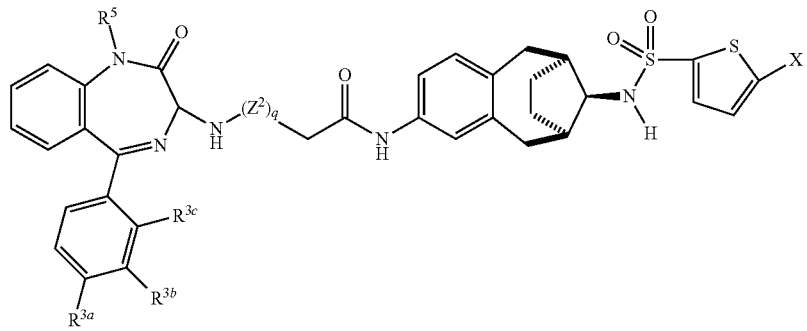

| Compound | X | $R^5$ | q | $Z^2$ | $R^{3a}$ | $R^{3b}$ | $R^{3c}$ |
|---|---|---|---|---|---|---|---|
| 285 | I | $CH_3$ | 0 | absent | H | H | H |
| 286 | I | $CH_3$ | 0 | absent | F | H | H |
| 287 | I | $CH_3$ | 0 | absent | H | F | H |
| 288 | I | $CH_3$ | 0 | absent | H | H | F |
| 289 | I | $CH_3$ | 0 | absent | $CH_3$ | H | H |
| 290 | I | $CH_3$ | 0 | absent | H | $CH_3$ | H |
| 291 | I | $CH_3$ | 0 | absent | H | H | $CH_3$ |
| 292 | I | $CH_3$ | 0 | absent | $CF_3$ | H | H |
| 293 | I | $CH_3$ | 0 | absent | H | $CF_3$ | H |
| 294 | I | $CH_3$ | 0 | absent | H | H | $CF_3$ |
| 295 | I | $CH_3$ | 1 | $CH_2$ | H | H | H |
| 296 | I | $CH_3$ | 1 | $CH_2$ | F | H | H |
| 297 | I | $CH_3$ | 1 | $CH_2$ | H | F | H |
| 298 | I | $CH_3$ | 1 | $CH_2$ | H | H | F |
| 299 | I | $CH_3$ | 1 | $CH_2$ | $CH_3$ | H | H |
| 300 | I | $CH_3$ | 1 | $CH_2$ | H | $CH_3$ | H |
| 301 | I | $CH_3$ | 1 | $CH_2$ | H | H | $CH_3$ |
| 302 | I | $CH_3$ | 1 | $CH_2$ | $CF_3$ | H | H |
| 303 | I | $CH_3$ | 1 | $CH_2$ | H | $CF_3$ | H |
| 304 | I | $CH_3$ | 1 | $CH_2$ | H | H | $CF_3$ | and the enantiomer having the Formula IIaaa', the enantiomer having the Formula IIaaa", and mixtures thereof, of each of Compounds 145-304, and pharmaceutically acceptable salts thereof The structures of Formulas IIaaa' and IIaaa" are depicted below:

Formula IIaaa'

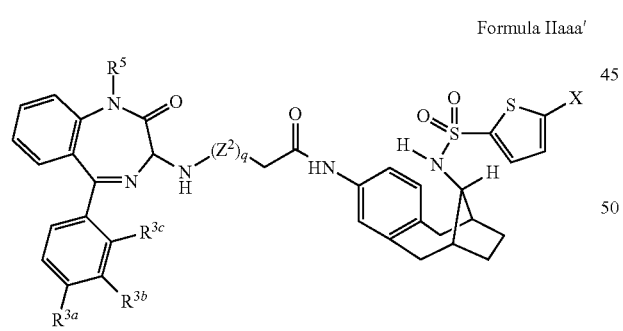

Formula IIaaa"

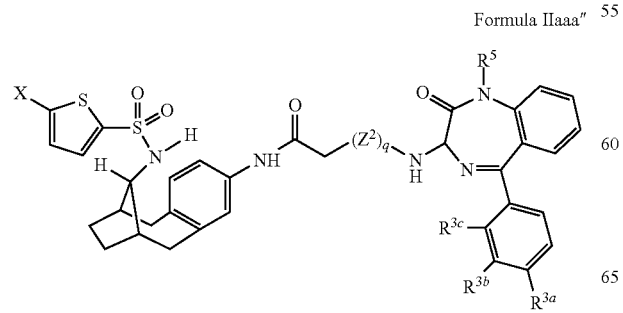

Formula IIaaa" is the corresponding opposite enantiomer of Formula IIaaa' when X, $R^5$, $Z^2$, q, $R^{3a}$, $R^{3b}$, and $R^{3c}$ of Formula IIaaa" are the same as X, $R^5$, $Z^2$, q, $R^{3a}$, $R^{3b}$, and $R^{3c}$ of Formula IIaaa'. Formula IIaaa' is the corresponding opposite enantiomer of Formula IIaaa" when X, $R^5$, $Z^2$, q, $R^{3a}$, $R^{3b}$, and $R^{3c}$ of Formula IIaaa' are the same as X, $R^5$, $Z^2$, q, $R^{3a}$, $R^{3b}$, and $R^{3c}$ of Formula IIaaa".

III. Methods for Making the Sulfonamide-Based Compounds

Methods useful for making the Sulfonamide-Based Compounds and pharmaceutically acceptable salts of Formula I are set forth in the Examples below and generalized in Scheme 1 below.

Scheme 1. Synthesis of Sulfonamide-Based Compounds of Formula I

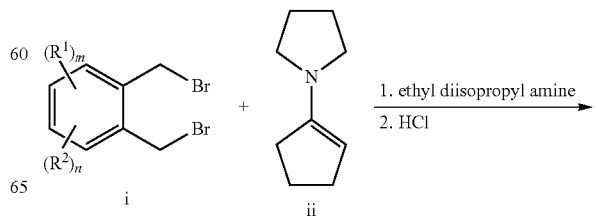

-continued

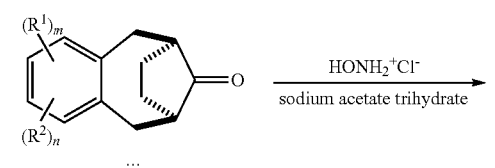
iii

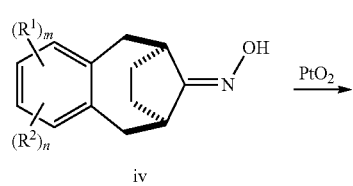
iv

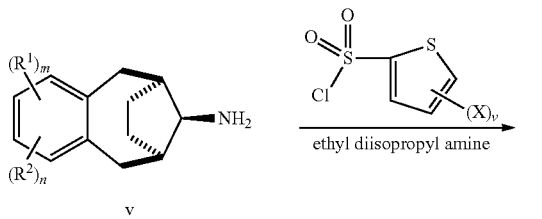
v

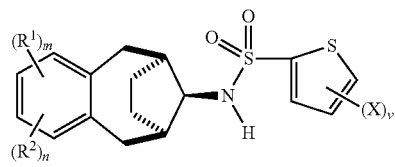
Formula I wherein R¹, R², X, m, n, and v are as defined above for the compounds or pharmaceutically acceptable salts of Formula I.

Methods useful for making the Sulfonamide-Based Compounds and pharmaceutically acceptable salts of Formula II are generalized in Scheme 2 below.

Scheme 2. Synthesis of Sulfonamide-Based Compounds of Formula I

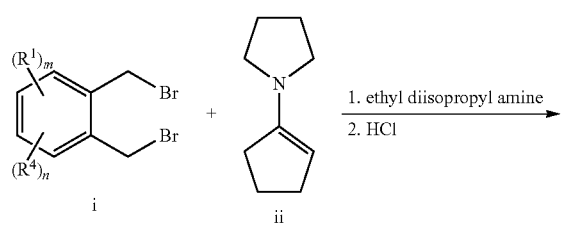
i             ii

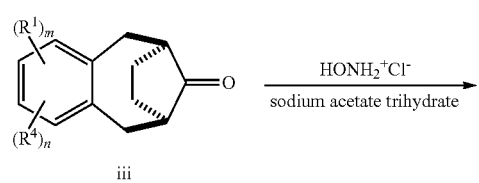
iii

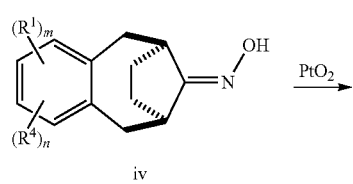
iv

-continued

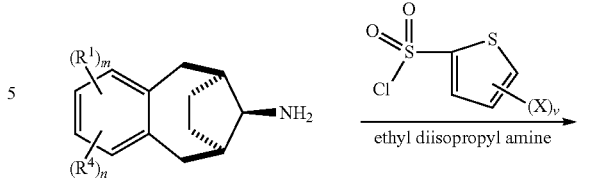
v

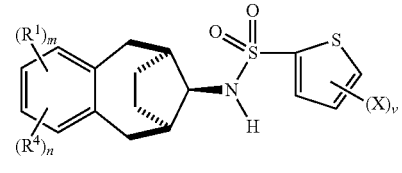
Formula II

Scheme 3a-b below provides a method for synthesizing a particular compound of Formula I or II where an appropriately substituted 1,2-bis(bromomethyl)benzene is not available as a starting material for preparation of the given compound according to Scheme 1 or 2. For instance, Scheme 3a is the synthesis and addition of $NO_2$ group to the benzobicyclo[4.2.1]nonane core.

Scheme 3a. Preparation and addition of $NO_2$ to benzobicyclo[4.2.1]nonane

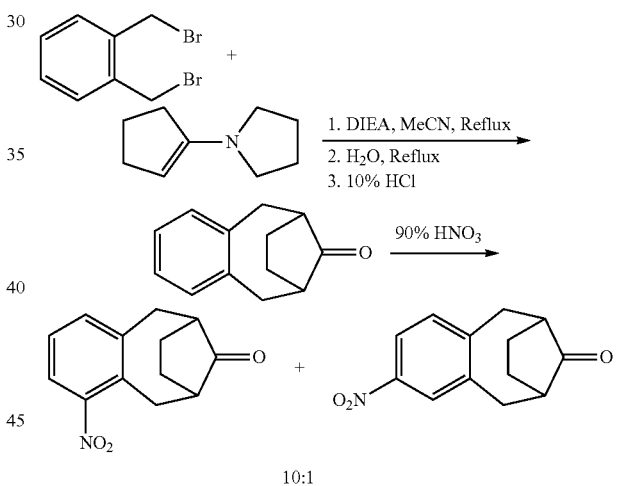

10:1

Scheme 3b exemplifies preparation of compounds of Formula I or II from nitrobenzobicyclo[4.2.1]nonane. R in Scheme 3b can be R² or R⁴ as defined above in the definitions for Formulas I and II, respectively.

Scheme 3b. Exemplary Preparation of Compounds of Formula I or II

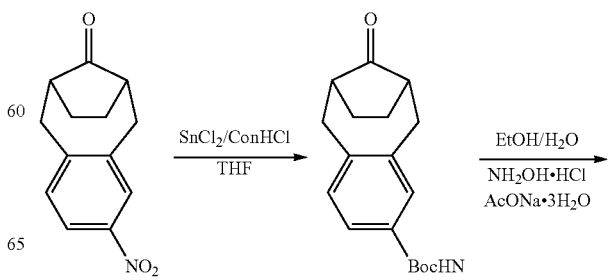

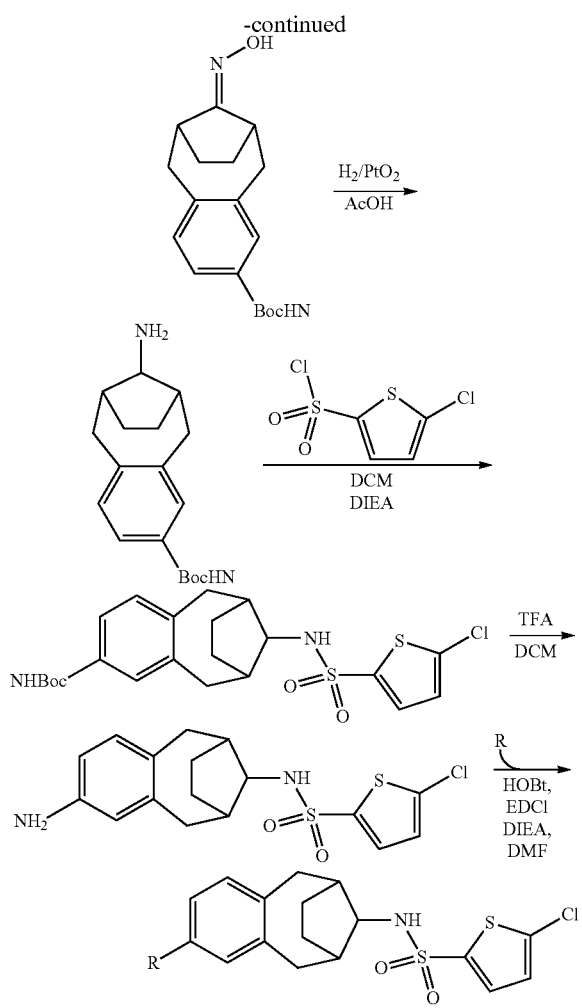

A Sulfonamide-Based Compound can be obtained, isolated, or purified such that it is substantially free of its corresponding opposite enantiomer using methods known to one of skill in the art, including chiral high performance liquid chromatography, selective crystallization, and reaction with a chiral resolving agent or chiral auxiliary.

IV. Treatment or Prevention of a Condition with the Sulfonamide-Based Compounds

In accordance with the invention, a Sulfonamide-Based Compound is useful for treating or preventing cancer or a neurodegenerative disease.

A. Treatment or Prevention of Cancer

The Sulfonamide-Based Compounds are useful for treating or preventing cancer. Accordingly, the invention provides methods for treating or preventing cancer, comprising administering an effective amount of a Sulfonamide-Based Compound to a subject. In one embodiment, the subject is in need of treatment or prevention of the cancer. In one embodiment, the methods further comprise administering an effective amount of another anticancer agent. Examples of cancers that the Sulfonamide-Based Compounds disclosed herein are useful for treating or preventing include, but are not limited to, the cancers disclosed below in Table 27 and metastases thereof.

TABLE 27

| Solid tumors, including but not limited to: | |
|---|---|
| fibrosarcoma | basal cell carcinoma |
| myxosarcoma | adenocarcinoma |
| liposarcoma | sweat gland carcinoma |
| chondrosarcoma | sebaceous gland carcinoma |
| osteogenic sarcoma | papillary carcinoma |
| chordoma | papillary adenocarcinomas |
| angiosarcoma | cystadenocarcinoma |
| endotheliosarcoma | medullary carcinoma |
| lymphangiosarcoma | bronchogenic carcinoma |
| lymphangioendotheliosarcoma | renal cell carcinoma |
| synovioma | hepatoma |
| mesothelioma | bile duct carcinoma |
| Ewing's tumor | choriocarcinoma |
| leiomyosarcoma | seminoma |
| rhabdomyosarcoma | embryonal carcinoma |
| colon cancer | Wilms' tumor |
| colorectal cancer | cervical cancer |
| kidney cancer | uterine cancer |
| pancreatic cancer | testicular cancer |
| bone cancer | small cell lung carcinoma |
| breast cancer | bladder carcinoma |
| ovarian cancer | lung cancer |
| prostate cancer | epithelial carcinoma |
| esophageal cancer | skin cancer |
| stomach cancer | melanoma |
| oral cancer | metastatic melanoma |
| nasal cancer | neuroblastoma |
| throat cancer | retinoblastoma |
| squamous cell carcinoma | |
| Blood-borne cancers, including but not limited to: | |
| acute lymphoblastic leukemia ("ALL") | acute myelomonocytic leukemia |
| acute lymphoblastic B-cell leukemia | acute nonlymphocyctic leukemia |
| acute lymphoblastic T-cell leukemia | acute undifferentiated leukemia |
| acute myeloblasts leukemia ("AML") | chronic myelocytic leukemia ("CML") |
| acute promyelocyte leukemia ("APL") | chronic lymphocytic leukemia ("CLL") |
| acute monoblastic leukemia | hairy cell leukemia |
| acute erythroleukemic leukemia | multiple myeloma |
| acute megakaryoblastic leukemia | |
| Acute and chronic leukemias, including but not limited to: | |
| lymphoblastic | lymphocytic |
| myelogenous | myelocytic leukemias |
| CNS and brain cancers, including but not limited to: | |
| glioma | acoustic neuroma |
| pilocytic astrocytoma | oligodendroglioma |
| astrocytoma | meningioma |
| anaplastic astrocytoma | vestibular schwannoma |
| glioblastoma multiforme | adenoma |
| medulloblastoma | metastatic brain tumor |
| craniopharyngioma | meningioma |
| ependymoma | spinal tumor |
| pinealoma | medulloblastoma |
| hemangioblastoma | |

In one embodiment, the cancer is lung cancer, breast cancer, colorectal cancer, prostate cancer, a leukemia, a lymphoma, non-Hodgkin's lymphoma, skin cancer, a brain cancer, a cancer of the central nervous system, ovarian cancer, uterine cancer, stomach cancer, pancreatic cancer, esophageal cancer, kidney cancer, liver cancer, or a head and neck cancer. In another embodiment, the cancer is metastatic cancer.

In yet another embodiment, the cancer is brain cancer or melanoma. In one embodiment, the brain cancer is metastatic brain cancer or a glioma. In one embodiment, the glioma is pilocytic astrocytoma, astrocytoma, anaplastic astrocytoma or glioblastoma multiforme. In one embodiment, the cancer is homologous-recombination deficient, such as BRCA-I or BRCA-2 deficient, or is deficient in one or more proteins of the Fanconi family. In one embodiment, the deficiency is caused by a genetic mutation. In another embodiment, the phenotype resulting from the deficiency is caused by abnormally low expression of BRCA-I or BRCA-2 protein. In another embodiment, the phenotype resulting from the deficiency is caused by abnormally low expression of one or more proteins of the Fanconi family.

In another embodiment, the cancer is leukemia, such as but not limited to, acute leukemia, acute lymphocytic leukemia, acute myelocytic leukemias, such as, myeloblastic, promyelocytic, myelomonocytic, monocytic, and erythroleukemia leukemias and myelodysplastic syndrome; chronic leukemia, such as but not limited to, chronic myelocytic (granulocytic) leukemia, chronic lymphocytic leukemia, hairy cell leukemia; polycythemia vera; lymphoma such as but not limited to Hodgkin's disease, non-Hodgkin's disease; multiple myeloma such as but not limited to smoldering multiple myeloma, nonsecretory myeloma, osteosclerotic myeloma, plasma cell leukemia, solitary plasmacytoma and extramedullary plasmacytoma; Waldenström's macroglobulinemia; monoclonal gammopathy of undetermined significance; benign monoclonal gammopathy; heavy chain disease; dendritic cell cancer, including plasmacytoid dendritic cell cancer, NK blastic lymphoma (also known as cutaneous NK/T-cell lymphoma and agranular (CD4+/CD56+) dermatologic neoplasms); basophilic leukemia; bone and connective tissue sarcomas such as but not limited to bone sarcoma, osteosarcoma, chondrosarcoma, Ewing's sarcoma, malignant giant cell tumor, fibrosarcoma of bone, chordoma, periosteal sarcoma, soft-tissue sarcomas, angiosarcoma (hemangiosarcoma), fibrosarcoma, Kaposi's sarcoma, leiomyosarcoma, liposarcoma, lymphangiosarcoma, neurilemmoma, rhabdomyosarcoma, synovial sarcoma; a brain tumor such as but not limited to, glioma, astrocytoma, brain stem glioma, ependymoma, oligodendroglioma, nonglial tumor, acoustic neurinoma, craniopharyngioma, medulloblastoma, meningioma, pineocytoma, pineoblastoma, primary brain lymphoma; breast cancer including but not limited to ductal carcinoma, adenocarcinoma, lobular (small cell) carcinoma, intraductal carcinoma, medullary breast cancer, mucinous breast cancer, tubular breast cancer, papillary breast cancer, Paget's disease, and inflammatory breast cancer; adrenal cancer such as but not limited to pheochromocytom and adrenocortical carcinoma; thyroid cancer such as but not limited to papillary or follicular thyroid cancer, medullary thyroid cancer and anaplastic thyroid cancer; pancreatic cancer such as but not limited to, insulinoma, gastrinoma, glucagonoma, vipoma, somatostatin-secreting tumor, and carcinoid or islet cell tumor; pituitary cancer such as but limited to Cushing's disease, prolactin-secreting tumor, acromegaly, and diabetes insipius; eye cancer such as but not limited to ocular melanoma such as iris melanoma, choroidal melanoma, and ciliary body melanoma, and retinoblastoma; vaginal cancer such as squamous cell carcinoma, adenocarcinoma, and melanoma; vulvar cancer such as squamous cell carcinoma, melanoma, adenocarcinoma, basal cell carcinoma, sarcoma, and Paget's disease; cervical cancer such as but not limited to, squamous cell carcinoma, and adenocarcinoma; uterine cancer such as but not limited to endometrial carcinoma and uterine sarcoma; ovarian cancer such as but not limited to, ovarian epithelial carcinoma, borderline tumor, germ cell tumor, and stromal tumor; esophageal cancer such as but not limited to, squamous cancer, adenocarcinoma, adenoid cystic carcinoma, mucoepidermoid carcinoma, adenosquamous carcinoma, sarcoma, melanoma, plasmacytoma, verrucous carcinoma, and oat cell (small cell) carcinoma; stomach cancer such as but not limited to, adenocarcinoma, fungating (polypoid), ulcerating, superficial spreading, diffusely spreading, malignant lymphoma, liposarcoma, fibrosarcoma, and carcinosarcoma; colon cancer; rectal cancer; liver cancer such as but not limited to hepatocellular carcinoma and hepatoblastoma; gallbladder cancer such as adenocarcinoma; cholangiocarcinomas such as but not limited to papillary, nodular, and diffuse; lung cancer such as non-small cell lung cancer, squamous cell carcinoma (epidermoid carcinoma), adenocarcinoma, large-cell carcinoma and small-cell lung cancer; testicular cancer such as but not limited to germinal tumor, seminoma, anaplastic, classic (typical), spermatocytic, nonseminoma, embryonal carcinoma, teratoma carcinoma, choriocarcinoma (yolk-sac tumor), prostate cancer such as but not limited to, prostatic intraepithelial neoplasia, adenocarcinoma, leiomyosarcoma, and rhabdomyosarcoma; penile cancer; oral cancer such as but not limited to squamous cell carcinoma; basal cancer; salivary gland cancer such as but not limited to adenocarcinoma, mucoepidermoid carcinoma, and adenoidcystic carcinoma; pharynx cancer such as but not limited to squamous cell cancer, and verrucous; skin cancer such as but not limited to, basal cell carcinoma, squamous cell carcinoma and melanoma, superficial spreading melanoma, nodular melanoma, lentigo malignant melanoma, acral lentiginous melanoma; kidney cancer such as but not limited to renal cell carcinoma, adenocarcinoma, hypernephroma, fibrosarcoma, transitional cell cancer (renal pelvis and/or uterer); Wilms' tumor; bladder cancer such as but not limited to transitional cell carcinoma, squamous cell cancer, adenocarcinoma, carcinosarcoma. In addition, cancer include myxosarcoma, osteogenic sarcoma, endotheliosarcoma, lymphangioendotheliosarcoma, mesothelioma, synovioma, hemangioblastoma, epithelial carcinoma, cystadenocarcinoma, bronchogenic carcinoma, sweat gland carcinoma, sebaceous gland carcinoma, papillary carcinoma and papillary adenocarcinomas (for a review of such disorders, see Fishman et al., 1985, Medicine, 2d Ed., J.B. Lippincott Co., Philadelphia and Murphy et al., 1997, Informed Decisions: The Complete Book of Cancer Diagnosis, Treatment, and Recovery, Viking Penguin, Penguin Books U.S.A., Inc., United States of America).

In a specific of this embodiment, the cancer is one that is associated with cleavage of notch by γ-secretase including, but not limited to, leukemia, non small cell lung cancer, ovarian cancer, breast cancer, or brain cancer.

In still another embodiment, the subject in need of treatment has previously undergone or is presently undergoing treatment for cancer. The treatment includes, but is not limited to, chemotherapy, radiation therapy, surgery or immunotherapy, such as administration of a cancer vaccine.

The Sulfonamide-Based Compounds are also useful for treating or preventing a cancer caused by a virus. Such viruses include human papilloma virus, which can lead to cervical cancer (see, e.g., Hernandez-Avila et al., *Archives of Medical Research* (1997) 28:265-271); Epstein-Barr virus (EBV), which can lead to lymphoma (see, e.g., Herrmann et al., *J. Pathol.* (2003) 199(2):140-5); hepatitis B or C virus, which can lead to liver carcinoma (see, e.g., El-Serag, *J. Clin. Gastroenterol.* (2002) 35(5 Suppl. 2):572-8); human T cell leukemia virus (HTLV)-I, which can lead to T-cell leukemia (see, e.g., Mortreux et al., *Leukemia* (2003) 17(1):26-38); human herpesvirus-8 infection, which can lead to Kaposi's sarcoma (see, e.g., Kadow et al., *Curr. Opin. Investig. Drugs* (2002) 3(11): 1574-9); and Human Immune deficiency Virus (HIV) infection, which can lead to cancer as a consequence of immunodeficiency (see, e.g., Dal Maso et al., Lancet Oncol (2003) 4(2): 110-9). Each of these references is incorporated herein by reference.

The Sulfonamide-Based Compounds are also useful for preventing cancer, or preventing progression of a cancer, including but not limited to the cancers listed in Table 27. Such prophylactic use includes that in which non-neoplastic cell growth such as hyperplasia, metaplasia, or most specifically, dysplasia has occurred. Alternatively or in addition to the presence of abnormal cell growth characterized as hyperplasia, metaplasia, or dysplasia, the presence of one or more characteristics of a transformed phenotype, or of a malignant phenotype, displayed in vivo or displayed in vitro by a cell sample from a subject, can indicate the desirability of prophylactic or therapeutic administration of a Sulfonamide-Based Compound. Such characteristics of a transformed phenotype include morphology changes, looser substratum attachment, loss of contact inhibition, loss of anchorage dependence, protease release, increased sugar transport, decreased serum requirement, expression of fetal antigens, disappearance of the 250,000 dalton cell surface protein, etc. In a specific embodiment, leukoplakia, a benign-appearing hyperplastic or dysplastic lesion of the epithelium, or Bowen's disease, a carcinoma in situ, is treatable or preventable according to the present methods.

In another embodiment, fibrocystic disease (cystic hyperplasia, mammary dysplasia, specifically adenosis (benign epithelial hyperplasia)) is treatable or preventable according to the present methods.

In other embodiments, a subject that has one or more of the following predisposing factors for malignancy can be treated by administration of an effective amount of a Sulfonamide-Based Compound: a chromosomal translocation associated with a malignancy (e.g., the Philadelphia chromosome for chronic myelogenous leukemia; t(14;18) for follicular lymphoma); familial polyposis or Gardner's syndrome; benign monoclonal gammopathy; a first degree kinship with persons having a cancer or precancerous disease showing a Mendelian (genetic) inheritance pattern (e.g., familial polyposis of the colon, Gardner's syndrome, hereditary exostosis, polyendocrine. adenomatosis, medullary thyroid carcinoma with amyloid production and pheochromocytoma, Peutz-Jeghers syndrome, neurofibromatosis of Von Recklinghausen, retinoblastoma, carotid body tumor, cutaneous melanocarcinoma, intraocular melanocarcinoma, xeroderma pigmentosum, ataxia telangiectasia, Chediak-Higashi syndrome, albinism, Fanconi's aplastic anemia, and Bloom's syndrome); and exposure to carcinogens (e.g., smoking, second-hand smoke exposure, and inhalation of or contacting with certain chemicals).

In one aspect, the present methods for treating or preventing cancer can further comprise the administration of another anticancer agent.

In one embodiment, the present invention provides methods for treating or preventing cancer, comprising the administration of an effective amount of a Sulfonamide-Based Compound and another anticancer agent to a subject in need thereof. The Sulfonamide-Based Compound and another anticancer agent can be administered concurrently. In this embodiment, the Sulfonamide-Based Compound and another anticancer agent can be administered within the same composition, or can be administered from different compositions, via the same or different routes of administration. In another embodiment, the Sulfonamide-Based Compound is administered during a time when the other anticancer agent exerts its prophylactic or therapeutic effect, or vice versa.

In another embodiment, the Sulfonamide-Based Compound or other anticancer agent is administered in doses commonly employed when such agents are used as monotherapy for the treatment of cancer.

In one embodiment, the Sulfonamide-Based Compound or other anticancer agent is administered in doses that are lower than the doses commonly employed when such agents are used as monotherapy for the treatment of cancer.

In another embodiment, the Sulfonamide-Based Compound and other anticancer agent act synergistically and are administered in doses that are lower than the doses commonly employed when such agents are used as monotherapy for the treatment of cancer. The dosage of the Sulfonamide-Based Compound or other anticancer agent administered as well as the dosing schedule can depend on various parameters, including, but not limited to, the cancer being treated, the subject's general health, and the administering physician's discretion. A Sulfonamide-Based Compound can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concurrently with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of the other anticancer agent, to a subject in need thereof. In various embodiments a Sulfonamide-Based Compound and the other anticancer agent are administered 1 minute apart, 10 minutes apart, 30 minutes apart, less than 1 hour apart, 1 hour apart, 1 hour to 2 hours apart, 2 hours to 3 hours apart, 3 hours to 4 hours apart, 4 hours to 5 hours apart, 5 hours to 6 hours apart, 6 hours to 7 hours apart, 7 hours to 8 hours apart, 8 hours to 9 hours apart, 9 hours to 10 hours apart, 10 hours to 11 hours apart, 11 hours to 12 hours apart, no more than 24 hours apart or no more than 48 hours apart. In one embodiment, a Sulfonamide-Based Compound and the other anticancer agent are administered within 3 hours. In another embodiment, a Sulfonamide-Based Compound and the other anticancer agent are administered at 1 minute to 24 hours apart.

In one embodiment, an effective amount of a Sulfonamide-Based Compound and an effective amount of other anticancer agent are present in the same composition. In one embodiment, this composition is useful for oral administration, in another embodiment, this composition is useful for intravenous administration.

In one embodiment, the compositions comprise an amount of a Sulfonamide-Based Compound and the other anticancer agent which together are effective to treat or prevent cancer.

In another embodiment, the compositions comprise an effective amount of temozolomide, procarbazine, dacarbazine, interleukin-2, irinotecan, or doxorubicin, a physiologically acceptable carrier, diluent, excipient, or vehicle, and an effective amount of a Sulfonamide-Based Compound.

In one embodiment, the amount of a Sulfonamide-Based Compound and the other anticancer agent is at least about 0.01% of the combined combination chemotherapy agents by weight of the composition. When intended for oral administration, this amount can be varied from about 0.1% to about 80% by weight of the composition. Some oral compositions can comprise from about 4% to about 50% of combined amount of a Sulfonamide-Based Compound and the other anticancer agent by weight of the composition. Other compositions of the present invention are prepared so that a parenteral dosage unit contains from about 0.01% to about 2% by weight of the composition.

Cancers that can be treated or prevented by administering a Sulfonamide-Based Compound and the other anticancer agent include, but are not limited to, the list of cancers set forth above in Table 27.

In one embodiment, the cancer is brain cancer. In specific embodiments, the brain cancer is pilocytic astrocytoma, astrocytoma, anaplastic astrocytoma, glioblastoma multiforme or a metastatic brain tumor.

In one embodiment, the cancer is melanoma. In a specific embodiment, the melanoma is metastatic melanoma.

The Sulfonamide-Based Compound and other anticancer agent can act additively or synergistically. A synergistic combination of a Sulfonamide-Based Compound and the other anticancer agent, might allow the use of lower dosages of one or both of these agents and/or less frequent administration of the agents to a subject with cancer. The ability to utilize lower dosages of one or both of the Sulfonamide-Based Compound and other anticancer agent and/or to administer the agents less frequently can reduce any toxicity associated with the administration of the agents to a subject without reducing the efficacy of the agents in the treatment of cancer. In addition, a synergistic effect might result in the improved efficacy of these agents in the treatment of cancer and/or the reduction of any adverse or unwanted side effects associated with the use of either agent alone.

In one embodiment, the administration of an effective amount of a Sulfonamide-Based Compound and an effective amount of another anticancer agent inhibits the resistance of a cancer to the other anticancer agent. In one embodiment, the cancer is a tumor.

Suitable other anticancer agents useful in the methods and compositions of the present invention include, but are not limited to temozolomide, a topoisomerase I inhibitor, procarbazine, dacarbazine, gemcitabine, capecitabine, methotrexate, taxol, taxotere, mercaptopurine, thioguanine, hydroxyurea, cytarabine, cyclophosphamide, ifosfamide, nitrosoureas, cisplatin, carboplatin, mitomycin, dacarbazine, procarbizine, etoposide, teniposide, campathecins, bleomycin, doxorubicin, idarubicin, daunorubicin, dactinomycin, plicamycin, mitoxantrone, L-asparaginase, doxorubicin, epirubicin, 5-fluorouracil, taxanes such as docetaxel and paclitaxel, leucovorin, levamisole, irinotecan, estramustine, etoposide, nitrogen mustards, BCNU, nitrosoureas such as carmustine and lomustine, vinca alkaloids such as vinblastine, vincristine and vinorelbine, platinum complexes such as cisplatin, carboplatin and oxaliplatin, imatinib mesylate, hexamethylmelamine, topotecan, tyrosine kinase inhibitors, tyrphostins herbimycin A, genistein, erbstatin, and lavendustin A.

In one embodiment, the other anticancer agent is, but is not limited to, a drug listed in Table 28.

TABLE 28

| Alkylating agents, including but not limited to: | | |
|---|---|---|
| Nitrogen mustards: | Cyclophosphamide | Trofosfamide |
|  | Ifosfamide | Chlorambucil |
| Nitrosoureas: | Carmustine (BCNU) | Lomustine (CCNU) |
| Alkylsulfonates: | Busulfan | Treosulfan |
| Triazenes: | Dacarbazine | Temozolomide |
|  | Procarbazine |  |
| Platinum containing | Cisplatin | Aroplatin |
| complexes: | Carboplatin | Oxaliplatin |
| Plant alkaloids, including but not limited to: | | |
| Vinca alkaloids: | Vincristine | Vindesine |
|  | Vinblastine | Vinorelbine |
| Taxoids: | Paclitaxel | Docetaxel |

TABLE 28-continued

| DNA topoisomerase inhibitors, including but not limited to: | | |
|---|---|---|
| Epipodophyllins: | Etoposide | 9-aminocamptothecin |
|  | Teniposide | Camptothecin |
|  | Topotecan | Crisnatol |
| Mitomycins: | Mitomycin C | Anti-metabolites |
| Anti-folates, including but not limited to: | | |
| DHFR inhibitors: | Methotrexate | Trimetrexate |
| IMP dehydrogenase | Mycophenolic acid | EICAR |
| inhibitors: | Tiazofurin | Ribavirin |
| Ribomiclotide | Deferoxamine | hydroxyurea |
| reductase inhibitors: | | |
| Pyrimidine analogs, including but not limited to: | | |
| Uracil analogs: | 5-Fluorouracil | Doxifluridine |
|  | Fluoxuridine | Ralitrexed |
| Cytosine analogs: | Cytarabine (ara C) | Gemcitabine |
|  | Cytosine arabinoside | Capecitabine |
|  | Fludarabine |  |
| Purine analogs: | Mercaptopurine | Thioguanine |
| DNA anti-metabolites: | 3-HP | beta-TGDR |
|  | 2'-deoxy-5-fluorouridine | cyclocytidine |
|  | 5-HP | guanazole |
|  | alpha-TGDR | inosine glycodialdehyde |
|  | aphidicolin | macebecin II |
|  | glycinate |  |
|  | ara-C | Pyrazoloimidazole |
|  | 5-aza-2'-deoxycytidine |  |
| Hormonal therapies, including but not limited to: | | |
| Receptor antagonists: | | |
| Anti-estrogen: | Tamoxifen | Megestrol |
|  | Raloxifene |  |
| LHRH agonists: | Goscrclin | Leuprolide acetate |
| Anti-androgens: | Flutamide | Bicalutamide |
| Retinoids/deltoids, including but not limited to: | | |
|  | Cis-retinoic acid |  |
| Vitamin A | All-trans retinoic |  |
| derivative: | acid (ATRA-IV) |  |
| Vitamin D3 analogs: | EB 1089 | KH 1060 |
|  | CB 1093 |  |
| Photodynamic therapies, including but not limited to: | | |
|  | Vertoporfin | Demethoxy-hypocrellin |
|  | (BPD-MA) | A |
|  | Plithalocyanine | (2BA-2-DMHA) |
|  | Photosensitizer Pc4 |  |
| Cytokines, including but not limited to: | | |
|  | Interferon-α | Tumor necrosis factor |
|  | Interferon-β | Interleukin-2 |
|  | Interferon-γ |  |
| Angiogenesis inhibitors, including but not limited to: | | |
|  | Angiostatin (plasminogen fragment) | MoAb IMC-IC1 1 |
|  | antiangiogenic antithrombin III | Neovastat |
|  | Angiozyme | NM-3 |
|  | ABT-627 | Panzem |
|  | Bay 12-9566 | PI-88 |
|  | Benefin | Placental ribonuclease inhibitor |
|  | Bevacizumab | Plasminogen activator inhibitor |
|  | BMS-275291 | Platelet factor-4 (PF4) |
|  | cartilage-derived inhibitor (CDI) | Prinomastat |
|  | CAI | Prolactin 16 kD fragment |
|  | CD59 complement fragment | Proliferin-related protein (PRP) |
|  | CEP-7055 | PTK 787/ZK 222594 |
|  | Col 3 | Retinoids |

TABLE 28-continued

| | | |
|---|---|---|
| Combretastatin A-4 | Solimastat | |
| Endostatin (collagen XVIII fragment) | Squalamine | |
| Fibronectin fragment | SS 3304 | |
| Gro-beta | SU 5416 | |
| Halofuginone | SU 6668 | |
| Heparinases | SUI 1248 | |
| Heparin hexa-saccharide fragment | Tetrahydrocortisol-S | |
| HMV833 | Tetrathiomolybdate | |
| Human chorionic gonadotropin (hCG) | Thalidomide | |
| IM-862 | Thrombospondin-1 (TSP-I) | |
| Interferon α/β/γ | TNP-470 | |
| Interferon inducible protein (IP-10) | Transforming growth factor-beta (TGF-β) | |
| Interleukin-12 | Vasculostatin | |
| Kringle 5 (plasminogen fragment) | Vasostatin (calreticulin fragment) | |
| Marimastat | ZD6126 | |
| Metalloproteinase inhibitors (TIMPs) | ZD 6474 | |
| 2-Methoxyestradiol | farnesyl transferase inhibitors (FTI) | |
| MMI 270 (CGS 27023 A) | Bisphosphonates | |
| Antimitotic agents, including but not limited to: | | |
| Allocolchicine | Maytansine | |
| Halichondrin B | Rhizoxin | |
| Colchicine | Thiocolchicine | |
| colchicine derivative | trityl cysteine | |
| dolstatin 10 | | |
| Others: | | |
| Isoprenylation inhibitors: | | |
| Dopaminergic neurotoxins: | 1-methyl-4-phenyl-pyridinium ion | |
| Cell cycle inhibitors: | Staurosporine | |
| Actinomycins: | Actinomycin D | Dactinomycin |
| Bleomycins: | Bleomycin A2 | Peplomycin |
| | Bleomycin B2 | |
| Anthracyclines: | Daunorubicin | Pirarabicin |
| | Doxorubicin (adriamycin) | Zorabicin |
| | Idarubicin | Mitoxantrone |
| | Epirubicin | |
| MDR inhibitors: | Verapamil | |
| Ca$^{2+}$ATPase inhibitors: | Thapsigargin | |

Other additional anticancer agents that are useful in the compositions and methods of the present invention include, but are not limited to: acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefmgol; chlorambucil; cirolemycin; cisplatin; cladribine; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; fluorocitabine; fosquidone; fostriecin sodium; gemcitabine hydrochloride; hydroxyurea; idarubicin hydrochloride; ifosfamide; ilmofosine; interleukin-2 (including recombinant interleukin-2, or rIL2), interferon alfa-2α; interferon alfa-2β; interferon alfa-n1; interferon alfa-n3; interferon beta-Iα; interferon γ-Iβ; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; paclitaxel; pegaspargase; peliomycin; pentamustine; peplomycin sulfate; perfosfamide; pipobroman; piposulfan; piroxantrone hydrochloride; plicamyciii; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; and zorubicin hydrochloride.

Further anticancer drugs that are useful in the methods and compositions of the invention include, but are not limited to: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta Lactam Derivatives; beta-alethine; betaclamycin B; betulinic acid; bFGF inhibitor; bicalutamide; bisantrene; bisaziridinylspermme; bisnafide; bistratene A; bizelesin; breflate; bropirimine; budotitane; buthionine sulfoximine; calcipotriol; calphostin C; camptothecin derivatives; canarypox IL-2; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin Analogue; conagenin; crambescidin 816; crisnatol; cryptopliycin 8; cryptophycin A derivatives; curacin A; cyclopentanthraquinones;

cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemniii B; didox; diethylnorspermine; dihydro-5-acytidine; dihydrotaxol; dioxamycin; diphenyl spiromustine; docetaxel; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine Analogue; lipophilic disaccharide peptide; lipophilic platinum complexes; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin Analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drag resistance gene inhibitor; multiple tumor suppressor 1-based therapy; mustard anticancer agents; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; 06-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel; paclitaxel Analogues; paclitaxel derivatives; palauamiiie; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum complexes; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; raboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen binding protein; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfm; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpuirt; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; ver amine; verdins; verteporfm; vinorelbine; vinxaltine; vitaxin; vorozole; zanoterone; zeniplatin; zilascorb; and zinostatin stimalamer.

In another embodiment, the other anticancer agent is interferon-α. In another embodiment, the other anticancer agent is interleukin-2. In one embodiment, the other anticancer agent is an alkylating agent, such as a nitrogen mustard, a nitrosourea, an alkylsulfonate, a triazene, or a platinum-containing agent. In one embodiment, the other anticancer agent is a triazene alkylating agent. In one embodiment, the other anticancer agent is O-6-benzylguanine. In another embodiment, the other anticancer agent is O-6-benzylguanine and temozolomide. In another embodiment, the other anticancer agent is O-6-benzylguanine and procarbazine. In still another embodiment, the other anticancer agent is O-6-benzylguanine and dacarbazine.

The Sulfonamide-Based Compounds can be administered to a subject that has undergone or is currently undergoing one or more additional anticancer therapies including, but not limited to, surgery, radiation therapy, or immunotherapy, such as cancer vaccines.

In one embodiment, the invention provides methods for treating or preventing cancer comprising administering to a subject in need thereof an effective amount of a Sulfonamide-Based Compound to treat or prevent cancer and another anticancer therapy including, but not limited to, surgery, radiation therapy, or immunotherapy, such as a cancer vaccine.

In one embodiment, the other anticancer therapy is radiation therapy. In another embodiment, the other anticancer therapy is surgery. In still another embodiment, the other anticancer therapy is immunotherapy.

In a specific embodiment, the present methods for treating or preventing cancer comprise administering an effective amount of a Sulfonamide-Based Compound and radiation therapy. The radiation therapy can be administered concurrently with, prior to, or subsequent to the Sulfonamide-Based Compound, in one embodiment at least an hour, five hours, 12 hours, a day, a week, a month, in another embodiment several months (e.g., up to three months), prior or subsequent to administration of the Sulfonamide-Based Compound. Where the other anticancer therapy is radiation therapy, any radiation therapy protocol can be administered depending upon the type of cancer to be treated. For example, but not by way of limitation, X-ray radiation can be administered; specifically, high-energy megavoltage (radiation of greater that 1 MeV energy) can be administered for deep tumors, and electron beam and orthovoltage X-ray radiation can be administered for skin cancers. Gamma-ray emitting radioisotopes, such as radioactive isotopes of radium, cobalt and other elements, can also be administered.

Additionally, the invention provides methods of treatment of cancer comprising administering a Sulfonamide-Based Compound as an alternative to chemotherapy or radiation therapy where the chemotherapy or the radiation therapy results in a negative side effect in the subject being treated. The subject being treated can, optionally, be treated with another anticancer therapy such as surgery, radiation therapy, or immunotherapy.

The Sulfonamide-Based Compounds can also be administered in vitro or ex vivo, such as for the treatment of certain cancers, including, but not limited to leukemias and lymphomas, such treatment involving autologous stem cell transplants. This can involve a process in which the subject's autologous hematopoietic stem cells are harvested and purged of all cancer cells, the subject's remaining bone-marrow cell population is then eradicated via the administration of a Sulfonamide-Based Compound and/or radiation, and the resultant stem cells are infused back into the subject. Supportive care can be subsequently provided while bone marrow function is restored and the subject recovers.

B. Treatment or Prevention of a Neurodegenerative Disease

The invention provides methods for treating or preventing a neurodegenerative disease, comprising administering an effective amount of a Sulfonamide-Based Compound to a subject. In one embodiment, the subject is in need treatment or prevention of the neurodegenerative disease. Examples of neurodegenerative diseases include, but are not limited to, Alexander's disease, Alper's disease, Alzheimer's disease, Amyotrophic lateral sclerosis ("ALS"), Ataxia telangiectasia. Batten disease (also known as Spielmeyer-Vogt-Sjogren-Batten disease), Bovine spongiform encephalopathy, Canavan disease, Cockayne syndrome, Corticobasal degeneration, Creutzfeldt-Jakob disease, Huntington's disease, HIV-associated dementia, Kennedy's disease, Krabbe's disease, Lewy body dementia, Machado-Joseph disease (Spinocerebellar ataxia type 3), Multiple sclerosis ("MS"), Multiple System Atrophy, Narcolepsy, Neuroborreliosis, Parkinson's disease, Pelizaeus-Merzbacher Disease, Pick's disease, Primary lateral sclerosis, Prion diseases, Progressive Supranuclear Palsy, Refsum's disease, Sandhoffs disease, Schilder's disease, Subacute combined degeneration of spinal cord secondary to Pernicious Anaemia, Spinocerebellar ataxia, Spinal muscular atrophy, Steele-Richardson-Olszewski disease, and Tabes dorsalis. In one embodiment, the neurodegenerative disease is Alzheimer's disease. Other examples of neurdegenerative diseases include, but are not limited to, diffuse Lewy body disease, multisystem degeneration (Shy-Drager syndrome), motor neuron diseases including amyotrophic lateral sclerosis, degenerative ataxias, cortical basal degeneration, ALS-Parkinson's-Dementia complex of Guam, subacute sclerosing panencephalitis, Huntington's disease, synucleinopathies, primary progressive aphasia, striatonigral degeneration, Machado-Joseph disease/spinocerebellar ataxia type 3 and olivopontocerebellar degenerations, Gilles De La Tourette's disease, bulbar and pseudobulbar palsy, spinal and spinobulbar muscular atrophy (Kennedy's disease), primary lateral sclerosis, familial spastic paraplegia, Werdnig-Hoffmann disease, Kugelberg-Welander disease, Tay-Sach's disease, Sandhoff disease, familial spastic disease, Wohifart-Kugelberg-Welander disease, spastic paraparesis, progressive multifocal leukoencephalopathy, prion diseases (including Creutzfeldt-Jakob, Gerstmann-Straussler-Scheinker disease, Kuru and fatal familial insomnia), age-related dementia and other conditions with memory loss, such as vascular dementia, diffuse white matter disease (Binswanger's disease), dementia of endocrine or metabolic origin, dementia of head trauma and diffuse brain damage, dementia pugilistica and frontal lobe dementia, cerebral ischemia or infaction including embolic occlusion and thrombotic occlusion as well as intracranial hemorrhage of any type (including, but not limited to, epidural, subdural, subarachnoid and intracerebral), and intracranial and intravertebral lesions (including, but not limited to, contusion, penetration, shear, compression and laceration).

In one aspect, the present methods for treating or preventing a neurodegenerative disease can further comprise the administration of another anti-neurodegenerative disease agent.

In one embodiment, the present invention provides methods for treating or preventing a neurodegenerative disease, comprising the administration of an effective amount of a Sulfonamide-Based Compound and another anti-neurodegenerative disease agent to a subject in need of treatment or prevention of the neurodegenerative disease. The Sulfonamide-Based Compound and another anti-neurodegenerative disease agent can be administered separately. The Sulfonamide-Based Compound and another anti-neurodegenerative disease agent can also be administered concurrently. In this embodiment, the Sulfonamide-Based Compound and another anti-neurodegenerative disease agent can be administered within the same composition, or can be administered from different compositions, via the same or different routes of administration. In another embodiment, the Sulfonamide-Based Compound is administered during a time when the other anti-neurodegenerative disease agent exerts its prophylactic or therapeutic effect, or vice versa.

In another embodiment, the Sulfonamide-Based Compound or other anti-neurodegenerative disease agent is administered in doses commonly employed when such agents are used as monotherapy for the treatment of a neurodegenerative disease.

In one embodiment, the Sulfonamide-Based Compound or other anti-neurodegenerative disease agent is administered in doses that are lower than the doses commonly employed when such agents are used as monotherapy for the treatment of a neurodegenerative disease.

In another embodiment, the Sulfonamide-Based Compound and other anti-neurodegenerative disease agent act synergistically and are administered in doses that are lower than the doses commonly employed when such agents are used as monotherapy for the treatment of a neurodegenerative disease. The dosage of the Sulfonamide-Based Compound or other anti-neurodegenerative disease agent administered as well as the dosing schedule can depend on various parameters, including, but not limited to, the neurodegenerative disease being treated, the subject's general health, and the administering physician's discretion. A Sulfonamide-Based Compound can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concurrently with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of the other anti-neurodegenerative disease agent, to a subject in need of treatment or prevention of the neurodegenerative disease. In various embodiments a Sulfonamide-Based Compound and the other anti-neurodegenerative disease agent are administered 1 minute apart, 10 minutes apart, 30 minutes apart, less than 1 hour apart, 1 hour apart, 1 hour to 2 hours apart, 2 hours to 3 hours apart, 3 hours to 4 hours apart, 4 hours to 5 hours apart, 5 hours to 6 hours apart, 6 hours to 7 hours apart, 7 hours to 8 hours apart, 8 hours to 9 hours apart, 9 hours to 10 hours apart, 10 hours to 11 hours apart, 11 hours to 12 hours apart, no more than 24 hours apart or no more than 48 hours apart. In one embodiment, a Sulfonamide-Based Compound and the other anti-neurodegenerative disease agent are administered within 3 hours. In another embodiment, a Sulfonamide-Based Compound and the other anti-neurodegenerative disease agent are administered at 1 minute to 24 hours apart.

In one embodiment, an effective amount of a Sulfonamide-Based Compound and an effective amount of other anti-neurodegenerative disease agent are present in the same composition. In one embodiment, this composition is useful for oral administration. In another embodiment, this composition is useful for intravenous administration.

In one embodiment, the compositions comprise an amount of a Sulfonamide-Based Compound and the other anti-neurodegenerative disease agent which together are effective to treat or prevent a neurodegenerative disease.

The Sulfonamide-Based Compound and other anti-neurodegenerative disease agent can act additively or synergistically. A synergistic combination of a Sulfonamide-Based Compound and the other anti-neurodegenerative disease agent, might allow the use of lower dosages of one or both of these agents and/or less frequent administration of the agents to a subject with a neurodegenerative disease. The ability to utilize lower dosages of one or both of the Sulfonamide-Based Compound and other anti-neurodegenerative disease agent and/or to administer the agents less frequently can reduce any toxicity associated with the administration of the agents to a subject without reducing the efficacy of the agents in the treatment of a neurodegenerative disease. In addition, a synergistic effect might result in the improved efficacy of these agents in the treatment of a neurodegenerative disease and/or the reduction of any adverse or unwanted side effects associated with the use of either agent alone.

In one embodiment, the administration of an effective amount of a Sulfonamide-Based Compound and an effective amount of another anti-neurodegenerative disease agent inhibits the resistance of a neurodegenerative disease to the other anti-neurodegenerative disease agent.

Suitable other anti-neurodegenerative disease agents useful in the methods and compositions of the present invention include, but are not limited to: anti-Alzheimer's agents, such as cholinesterase inhibitors (e.g., tacrine, donepezil hydrochloride, rivastigmine, or galantamine) or partial glutamate antagonists (e.g., memantine); anti-Parkinson's agents, such as levodopa, carbidopa, tolcapone, bromocriptine, pergolide, pramipexole, ropinirole, selegiline, or amantadine; anti-ALS agents, such as riluzole; and anti-MS agents, such as interferon beta-1a, interferon beta-1b, glatiramer acetate, mitoxantrone, or natalizumab.

C. Combination Therapy

Additional agents that can be used in a combination product with Sulfonamide-Based Compounds for the treatment or prevention of diseases associated with γ-secretase activity or prevention of diseases associated with γ-secretase activity include, but are not limited to, a small molecule, a synthetic drug, a peptide (including a cyclic peptide), a polypeptide, a protein, a nucleic acid (e.g., a DNA and RNA nucleotide including, but not limited to, an antisense nucleotide sequence, a triple helix, RNAi, and a nucleotide sequence encoding a biologically active protein, polypeptide or peptide), an antibody, a synthetic or natural inorganic molecule, a mimetic agent, and a synthetic or natural organic molecule. Specific examples of such agents include, but are not limited to, an immunomodulatory agent (e.g., interferon), anti-inflammatory agent (e.g., an adrenocorticoid, a corticosteroid (e.g., beclomethasone, budesonide, flunisolide, fluticasone, triamcinolone, methylprednisolone, prednisolone, prednisone, hydrocortisone), a glucocorticoid, a steroid, and a non-steriodal anti-inflammatory drug (e.g., aspirin, ibuprofen, diclofenac, and a COX-2 inhibitor), a pain reliever, a leukotreine antagonist (e.g., montelukast, a methyl xanthine, zafirlukast, and zileuton), a beta2-agonist (e.g., albuterol, biterol, fenoterol, isoetharie, metaproterenol, pirbuterol, salbutamol, terbutalin formoterol, salmeterol, and salbutamol terbutaline), an anticholinergic agent (e.g., ipratropium bromide and oxitropium bromide), sulphasalazine, penicillamine, dapsone, an antihistamine, an anti-malarial agent (e.g., hydroxychloroquine), an anti-viral agent (e.g., a nucleoside analog (e.g., zidovudine, acyclovir, gangcyclovir, vidarabine, idoxuridine, trifluridine, and ribavirin), foscarnet, amantadine, rimantadine, saquinavir, indinavir, ritonavir, and AZT) and an antibiotic (e.g., dactinomycin (formerly actinomycin), bleomycin, erythomycin, penicillin, mithramycin, and anthramycin (AMC)).

Any therapy which is known to be useful, or which has been used, will be used or is currently being used for the treatment or prevention of diseases associated with γ-secretase activity can be used in combination with the Sulfonamide-Based Compounds in accordance with the invention described herein.

V. Therapeutic or Prophylactic Administration and Compositions of the Invention

Due to their activity, Sulfonamide-Based Compounds are advantageously useful in veterinary and human medicine. As described above, the Sulfonamide-Based Compounds are useful for treating or preventing cancer or a neurodegenerative disease in a subject, including a subject that is in need of treatment or prevention of the cancer or neurodegenerative disease. Without being bound by theory, it is believed that the Sulfonamide-Based Compounds exert their therapeutic or prophylactic effect by inhibiting γ-secretase.

The Sulfonamide-Based Compounds can be administered in amounts that are effective to treat or prevent cancer or a neurodegenerative disease in a subject in need of treatment or prevention of the neurodegenerative disease.

When administered to a subject, the Sulfonamide-Based Compounds can be administered as a component of a composition that comprises a pharmaceutically acceptable carrier, diluent, excipient, or vehicle. The present compositions, which comprise a Sulfonamide-Based Compound, can be administered orally. The Sulfonamide-Based Compounds can also be administered by any other convenient route, for example, by infusion or bolus injection, by absorption through epithelial or mucocutaneous linings (e.g., oral, rectal, or intestinal mucosa) and can be administered together with another biologically active agent. Administration can be systemic or local. Various delivery systems are known, e.g., encapsulation in liposomes, microparticles, microcapsules and capsules.

Methods of administration include, but are not limited to, intradermal, intramuscular, intraperitoneal, intravenous, subcutaneous, intranasal, epidural, oral, sublingual, intracerebral, intravaginal, transdermal, rectal, by inhalation, or topical, specifically to the ears, nose, eyes, or skin. In some instances, administration will result in the release of a Sulfonamide-Based Compound into the bloodstream.

In one embodiment, the Sulfonamide-Based Compounds are administered orally. In other embodiments, it can be desirable to administer the Sulfonamide-Based Compounds locally. This can be achieved, for example, and not by way of limitation, by local infusion during surgery, topical application, e.g., in conjunction with a wound dressing after surgery, by injection, by means of a catheter, by means of a suppository or enema, or by means of an implant, said implant being of a porous, non-porous, or gelatinous material, including membranes, such as sialastic membranes, or fibers.

In certain embodiments, it can be desirable to introduce the Sulfonamide-Based Compounds into the central nervous system or gastrointestinal tract by any suitable route, including intraventricular, intrathecal, and epidural injection, and enema. Intraventricular injection can be facilitated by an intraventricular catheter, for example, attached to a reservoir, such as an Ommaya reservoir.

Pulmonary administration can also be employed, e.g., by use of an inhaler of nebulizer, and formulation with an aerosolizing agent, or via perfusion in a fluorocarbon oar, synthetic pulmonary surfactant. In certain embodiments, the Sulfonamide-Based Compounds can be formulated as a suppository, with traditional binders and excipients such as triglycerides.

In another embodiment Sulfonamide-Based Compounds can be delivered in a vesicle, specifically a liposome (see Langer, *Science* 249:1527-1533 (1990) and Liposomes in Therapy of Infectious Disease and Cancer 317-327 and 353-365 (1989)).

In yet another embodiment, the Sulfonamide-Based Compounds can be delivered in a controlled-release system or sustained-release system (see, e.g., Goodson, in Medical Applications of Controlled Release, supra, vol. 2, pp. 115-138 (1984)). Other controlled or sustained-release systems discussed in the review by Langer, Science 249: 1527-1533 (1990) can be used. In one embodiment a pump can be used (Langer, Science 249: 1527-1533 (1990); Sefton, *CRC Crit. Ref Biomed. Eng.* 14:201 (1987); Buchwald et al, Surgery 88:507 (1980); and Saudek et al., N. *Engl. J Med.* 321:574 (1989)). In another embodiment polymeric materials can be used (see Medical Applications of Controlled Release (Langer and Wise eds., 1974); Controlled Drug Bioavailability, Drug Product Design and Performance (Smolen and Ball eds., 1984); Ranger and Peppas, *J. Macromol. Sd. Rev. Macromol. Chem.* 2:61 (1983); Levy et al, *Science* 228:190 (1935); During et al, *Ann. Neural.* 25:351 (1989); and Howard et al, *J. Neurosurg.* 71:105 (1989)).

In yet another embodiment a controlled- or sustained-release system can be placed in proximity of a target of the Sulfonamide-Based Compounds, e.g., the spinal column, brain, skin, lung, or gastrointestinal tract, thus requiring only a fraction of the systemic dose.

The present compositions can optionally comprise a suitable amount of a pharmaceutically acceptable excipient so as to provide the form for proper administration to the subject.

Such pharmaceutical excipients can be liquids, such as water and oils, including those of petroleum, animal, vegetable, or synthetic origin, such as peanut oil, soybean oil, mineral oil, sesame oil and the like. The pharmaceutical excipients can be saline, gum acacia, gelatin, starch paste, talc, keratin, colloidal silica, urea and the like. In addition, auxiliary, stabilizing, thickening, lubricating, and coloring agents can be used. In one embodiment, the pharmaceutically acceptable excipients are sterile when administered to a subject. Water is a useful excipient when the Sulfonamide-Based Compound is administered intravenously. Saline solutions and aqueous dextrose and glycerol solutions can also be employed as liquid excipients, specifically for injectable solutions. Suitable pharmaceutical excipients also include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The present compositions, if desired, can also contain minor amounts of wetting or emulsifying agents, or pH buffering agents.

The present compositions can take the form of solutions, suspensions, emulsion, tablets, pills, pellets, capsules, capsules containing liquids, powders, sustained-release formulations, suppositories, emulsions, aerosols, sprays, suspensions, or any other form suitable for use. In one embodiment, the composition is in the form of a capsule (see e.g. U.S. Pat. No. 5,698,155). Other examples of suitable pharmaceutical excipients are described in Remington's Pharmaceutical Sciences 1447-1676 (Alfonso R. Gennaro eds., 19th ed. 1995), incorporated herein by reference.

In one embodiment, the Sulfonamide-Based Compound is formulated in accordance with routine procedures as a composition adapted for oral administration to human beings. Compositions for oral delivery can be in the form of tablets, lozenges, aqueous or oily suspensions, granules, powders, emulsions, capsules, syrups, or elixirs for example. Orally administered compositions can contain one or more agents, for example, sweetening agents such as fructose, aspartame or saccharin; flavoring agents such as peppermint, oil of wintergreen, or cherry; coloring agents; and preserving agents, to provide a pharmaceutically palatable preparation. Moreover, where in tablet or pill form, the compositions can be coated to delay disintegration and absorption in the gastrointestinal tract thereby providing a sustained action over an extended period of time. Selectively permeable membranes surrounding an osmotically active driving a Sulfonamide-Based Compound are also suitable for orally administered compositions. In these latter platforms, fluid from the environment surrounding the capsule is imbibed by the driving compound, which swells to displace the agent or agent composition through an aperture. These delivery platforms can provide an essentially zero order delivery profile as opposed to the spiked profiles of immediate release formulations. A time-delay material such as glycerol monostearate or glycerol stearate can also be useful. Oral compositions can include standard excipients such as mannitol, lactose, starch, magnesium stearate, sodium saccharin, cellulose, and magnesium carbonate. In one embodiment, the excipients are of pharmaceutical grade.

In another embodiment, the Sulfonamide-Based Compounds can be formulated for intravenous administration. Typically, compositions for intravenous administration comprise sterile isotonic aqueous buffer. Where necessary, the compositions can also include a solubilizing agent. Compositions for intravenous administration can optionally include a local anesthetic such as lignocaine to lessen pain at the site of the injection.

Generally, the ingredients are supplied either separately or mixed together in unit dosage form, for example, as a dry lyophilized-powder or water-free concentrate in a hermetically sealed container such as an ampule or sachette indicating the quantity of active agent. Where the Sulfonamide-Based Compounds are to be administered by infusion, they can be dispensed, for example, with an infusion bottle containing sterile pharmaceutical grade water or saline. Where the Sulfonamide-Based Compounds are administered by injection, an ampule of sterile water for injection or saline can be provided so that the ingredients can be mixed prior to administration.

Sulfonamide-Based Compounds can be administered by controlled-release or sustained-release means or by delivery devices that are well known to those of ordinary skill in the art. Examples include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; and 5,733,556, each of which is incorporated herein by reference in its entirety. Such dosage forms can be useful for providing controlled- or sustained-release of one or more active ingredients using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. Suitable controlled- or sustained-release formulations known to those skilled in the art, including those described herein, can be readily selected for use with the active ingredients of the invention. The invention thus provides single unit dosage forms suitable for oral administration such as, but not limited to, tablets, capsules, gelcaps, and caplets that are adapted for controlled- or sustained-release.

In one embodiment a controlled- or sustained-release composition comprises a minimal amount of a Sulfonamide-Based Compound to treat or prevent the neurodegenerative disease over a period of time. Advantages of controlled- or sustained-release compositions include extended activity of the drug, reduced dosage frequency, and increased subject compliance. In addition, controlled- or sustained-release compositions can favorably affect the time of onset of action or other characteristics, such as blood levels of the Sulfonamide-Based Compound, and can thus reduce the occurrence of adverse side effects. Controlled- or sustained-release compositions can initially release an amount of a Sulfonamide-Based Compound that promptly produces the desired therapeutic or prophylactic effect, and gradually and continually release other amounts of the Sulfonamide-Based Compound to maintain this level of therapeutic or prophylactic effect over an extended period of time. To maintain a constant level of the Sulfonamide-Based Compound in the body, the Sulfonamide-Based Compound can be released from the dosage form at a rate that will replace the amount of Sulfonamide-Based Compound being metabolized and excreted from the body.

Controlled- or sustained-release of an active ingredient can be stimulated by various conditions, including but not limited to, changes in pH, changes in temperature, concentration or availability of enzymes, concentration or availability of water, or other physiological conditions or compounds. The amount of the Sulfonamide-Based Compounds that is effective in the treatment or prevention of a neurodegenerative disease can be determined by standard clinical techniques. In addition, in vitro or in vivo assays can optionally be employed to help identify optimal dosage ranges. The precise dose to be employed can also depend on the route of administration, and the seriousness of the condition being treated and can be decided according to the judgment of the practitioner and each subject's circumstances in view of, e.g., published clinical studies. Suitable effective dosage amounts, however, range from about 10 micrograms to about 5 grams about every 4 hours, although they are typically about 500 mg or less per every 4 hours. In one embodiment, the effective dosage is about 0.01 mg, 0.5 mg, about 1 mg, about 50 mg, about 100 mg, about 200 mg, about 300 mg, about 400 mg, about 500 mg, about 600 mg, about 700 mg, about 800 mg, about 900 mg, about 1 g, about 1.2 g, about 1.4 g, about 1.6 g, about 1.8 g, about 2.0 g, about 2.2 g, about 2.4 g, about 2.6 g, about 2.8 g, about 3.0 g, about 3.2 g, about 3.4 g, about 3.6 g, about 3.8 g, about 4.0 g, about 4.2 g, about 4.4 g, about 4.6 g, about 4.8 g, and about 5.0 g, every 4 hours. Equivalent dosages can be administered over various time periods including, but not limited to, about every 2 hours, about every 6 hours, about every 8 hours, about every 12 hours, about every 24 hours, about every 36 hours, about every 48 hours, about every 72 hours, about every week, about every two weeks, about every three weeks, about every month, and about every two months. The effective dosage amounts described herein refer to total amounts administered; that is, if more than one Sulfonamide-Based Compound is administered, the effective dosage amounts correspond to the total amount administered.

Compositions can be prepared according to conventional mixing, granulating or coating methods, respectively, and the present compositions can contain, in one embodiment, from about 0.1% to about 99%; and in another embodiment from about 1% to about 70% of the Sulfonamide-Based Compound by weight or volume.

The dosage regimen utilizing the Sulfonamide-Based Compound can be selected in accordance with a variety of factors including type, species, age, weight, sex and medical condition of the subject; the severity of the condition to be treated; the route of administration; the renal or hepatic function of the subject; and the specific Sulfonamide-Based Compound employed. A Sulfonamide-Based Compound can be administered in a single daily dose, or the total daily dosage can be administered in divided doses of two, three or four times daily. Furthermore, a Sulfonamide-Based Compound can be administered in intranasal form via topical use of suitable intranasal vehicles, or via transdermal routes, using those forms of transdermal skin patches well known to those of ordinary skill in that art. To be administered in the form of a transdermal delivery system, the dosage administration can be continuous rather than intermittent throughout the dosage regimen. Other illustrative topical preparations include creams, ointments, lotions, aerosol sprays and gels, wherein the concentration of Sulfonamide-Based Compound ranges from about 0.1% to about 15%, w/w or w/v. The Sulfonamide-Based Compounds can be assayed in vitro or in vivo for the desired therapeutic or prophylactic activity prior to use in humans. Animal model systems can be used to demonstrate safety and efficacy.

In certain embodiments, a Sulfonamide-Based Compound or pharmaceutical composition thereof is administered to a human that has an age in a range of from about 0 months to about 6 months old, from about 6 to about 12 months old, from about 6 to about 18 months old, from about 18 to about 36 months old, from about 1 to about 5 years old, from about 5 to about 10 years old, from about 10 to about 15 years old, from about 15 to about 20 years old, from about 20 to about 25 years old, from about 25 to about 30 years old, from about 30 to about 35 years old, from about 35 to about 40 years old, from about 40 to about 45 years old, from about 45 to about 50 years old, from about 50 to about 55 years old, from about 55 to about 60 years old, from about 60 to about 65 years old, from about 65 to about 70 years old, from about 70 to about 75 years old, from about 75 to about 80 years old, from about 80 to about 85 years old, from about 85 to about 90 years old, from about 90 to about 95 years old or from about 95 to about 100 years old.

In some embodiments, a Sulfonamide-Based Compound or pharmaceutical composition thereof is administered to a human infant. In other embodiments, a Sulfonamide-Based Compound or pharmaceutical composition thereof is administered to a human toddler. In other embodiments, a Sulfonamide-Based Compound or pharmaceutical composition thereof is administered to a human child. In other embodiments, a Sulfonamide-Based Compound or pharmaceutical composition thereof is administered to a human adult. In yet other embodiments, a Sulfonamide-Based Compound or pharmaceutical composition thereof is administered to an elderly human.

In certain embodiments, a Sulfonamide-Based Compound or pharmaceutical composition thereof is administered a subject in an immunocompromised state or immunosuppressed state or at risk for becoming immunocompromised or immunosuppressed. In certain embodiments, a Sulfonamide-Based Compound or pharmaceutical composition thereof is administered to a subject receiving or recovering from immunosuppressive therapy.

In some embodiments, a Sulfonamide-Based Compound or pharmaceutical composition thereof is administered to a patient who is susceptible to adverse reactions to conventional anti-γ-secretase therapies. In some embodiments, a γ-secretase inhibitor or pharmaceutical composition thereof is administered to a patient who has proven refractory to anti-γ-secretase therapies other than γ-secretase inhibitors, but are no longer on these therapies. Among these patients are refractory patients, and patients who are too young for conventional therapies.

In some embodiments, the subject being administered a Sulfonamide-Based Compound or pharmaceutical composition thereof has not received therapy prior to the administration of the Sulfonamide-Based Compound or pharmaceutical composition thereof.

VI. Kits Comprising a Sulfonamide-Based Compound

The invention provides kits that can simplify the administration of a Sulfonamide-Based Compound to a subject.

A typical kit of the invention comprises a unit dosage form of a Sulfonamide-Based Compound. In one embodiment, the unit dosage form is a container, which can be sterile, containing an effective amount of a Sulfonamide-Based Compound and a pharmaceutically acceptable carrier, diluent, excipient, or vehicle. The kit can further comprise a label or printed instructions instructing the use of the Sulfonamide-Based Compound to treat or prevent a neurodegenerative disease. The kit can also further comprise a unit dosage form of another prophylactic or therapeutic agent, for example, a container containing an effective amount of the other prophylactic or therapeutic agent. In one embodiment, the kit comprises a container containing an effective amount of a Sulfonamide-Based Compound and an effective amount of another prophylactic or therapeutic agent. Examples of other prophylactic or therapeutic agents include, but are not limited to, those listed above.

The invention is further defined by reference to the following examples.

EXAMPLES

Example 1

Synthesis of endo-5-chloro-thiophene-2-sulfonic acid (tricyclo[8.2.1.0]trideca-3(8),4,6-trien-13-yl)-amide Step A: Synthesis of 11-oxo-5,6,7,8,9,10-hexahydro-6,9-methanobenzocyclooctene

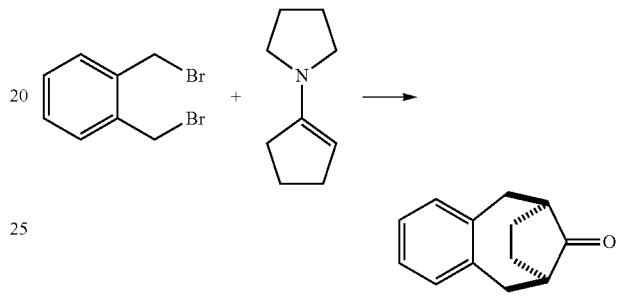

Ethyl diisopropylamine (10.3 g, 13.9 mL, 79.8 mmol) and a solution of 1-pyrrolidino-1-cyclopentene (5.2 g, 5.5 mL, 37.8 mmol) in acetonitrile (75 mL) were added successively to a vigorously stirred solution of α,α'-dibromo-o-xylene (10.0 g, 38.0 mmol) in acetonitrile (75 mL) and the resultant mixture was heated to reflux under nitrogen for 18 hours. Water (75 mL) was added and the mixture was heated for an addition 1 hour. Then the solution was cooled and 10% hydrochloric acid (38 mL) was added. Most of the volatiles were removed in vacuo, and the resultant residue was extracted with ether (4×100 mL). The combined ethereal extracts were washed successively with brine, dried (Na$_2$SO$_4$), filtered, and concentrated. The concentrate was purified using flash column chromatography ("FCC") to provide 11-oxo-5,6,7,8,9, 10-hexahydro-6,9-methanobenzocyclooctene (5.1 g, 72%).

Step B: Synthesis of tricyclo[8.2.1.0]trideca-3(8),4,6-trien-13-one oxime

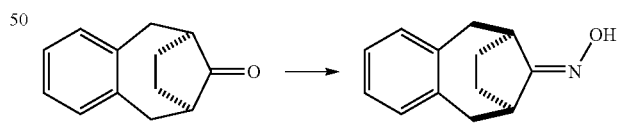

11-oxo-5,6,7,8,9,10-hexahydro-6,9-methanobenzocyclooctene (2.3 g, 12.4 mmol) was suspended in EtOH (16.5 mL) and H$_2$O (8.3 mL) and stirred. Hydroxylamine hydrochloride (2.6 g, 37.1 mmol) was added to the suspension, resulting in the dissolution of the 11-oxo-5,6,7,8,9,10-hexahydro-6,9-methanobenzocyclooctene. Sodium acetate trihydrate (4.6 g, 33.8 mmol) was then added to the resultant solution. After a few minutes, a thick white precipitate formed. The resultant mixture was heated to reflux until a clear solution was obtained, and then allowed to cool to room temperature. The product tricyclo[8.2.1.0]trideca-3(8),4,6-trien-13-one oxime crystallized from the solution and the crystals were collected by filtration. The crystals were then washed with water and dried to provide tricyclo[8.2.1.0]trideca-3(8),4,6-trien-13-one oxime 2.4 g (99%) as a pure white crystalline solid.

Step C: Synthesis of endo-tricyclo[8.2.1.0]trideca-3(8),4,6-trien-13-ylamine

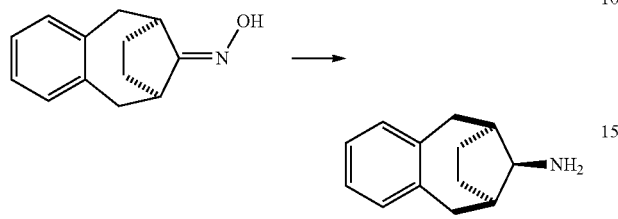

Tricyclo[8.2.1.0]trideca-3(8),4,6-trien-13-one oxime (250 mg, 1.2 mmol) was dissolved in acetic acid (2 mL). PtO$_2$ (1 5 mg) was added to the solution, and the resultant mixture was hydrogenated for 18 hours. The mixture was filtered through Celite®, washing with acetic acid, and the filtrate was concentrated to provide endo-tricyclo[8.2.1.0]trideca-3(8),4,6-trien-13-ylamine as a white solid, which was used in Step D without further purification.

Step D: Synthesis of endo-5-chloro-thiophene-2-sulfonic acid (tricyclo[8.2.1.0]trideca-3(8),4,6-trien-13-yl)-amide

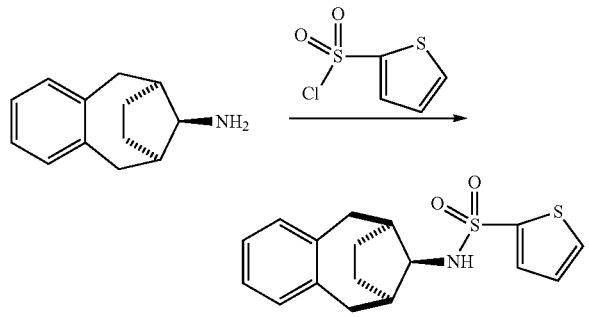

The endo-tricyclo[8.2.1.0]trideca-3(8),4,6-trien-13-ylamine from Step D was dissolved in CH$_2$Cl$_2$ (7 mL) and treated with ethyl diisopropylamine (384.4 mg, 2.9 mmol, 0.5 mL) and 2-thiophenesulfonyl chloride (270 mg, 1.5 mmol). The resultant mixture was stirred for 16 hours, and then concentrated in vacuo. The concentrate was purified using FCC to provide endo-5-chloro-thiophene-2-sulfonic acid (tricyclo[8.2.1.0]trideca-3(8),4,6-trien-13-yl)-amide (107.7 mg, 26% from endo-tricyclo[8.2.1.0]trideca-3(8),4,6-trien-13-ylamine).

Example 2

In Vitro Inhibition of γ-Secretase Activity

Without being bound by theory, it is believed that inhibiting γ-secretase activity, including that which generates Aβ40, is desirable for the treatment or prevention of a neurodegenerative disease, particularly Alzheimer's disease.

Several of the above-described Sulfonamide-Based Compounds show in vitro inhibition of γ-secretase activity that generates A1340. IC$_{50}$ values for inhibition of the generation of Aβ40 were measured. The results of these studies are summarized below in Table 3.

The assay protocol employed was a modified version of that described in Li et al., 2000, Proc. Nat'l Acad. Sci. USA 97:6183-643, incorporated herein by reference. Briefly, recombinant peptide substrate was incubated with γ-secretase (40 μg/ml) in the presence or absence of test compound. The reaction mixture contained 0.25% CHAPSO, 0.1 μg/μl BSA, protease inhibitor, 50 mM PIPES, pH 7.0, 5 mM MgCl$_2$, 5 mM CaCl$_2$ and 150 mM KCl. The reaction was incubated for 2.5 hr at 37° C. and stopped by adding RIPA buffer (150 mM NaCl, 1.0% NP-40, 0.5% sodium deoxycholate, 0.1% SDS, 50 mM Tris HCl, pH 8.0). The products were detected with various antibody combinations using electrochemiluminescence (ECL) technology as previously described in Li et al., 2000, Proc. Nat'l Acad. Sci. USA 97:6183-643; Lai et al., 2003, J. Biol. Chem. 278: 22475-22481; and Yin et al., 2007, J. Biol. Chem. 282:23639-23644. The amount of product was determined using synthetic peptide or recombinant standards.

TABLE 3

In vitro inhibition of γ-secretase activity for Sulfonamide-Based Compounds

| Compound | Chemical Structure | IC$_{50}$ (μM) |
|---|---|---|
| 5 | 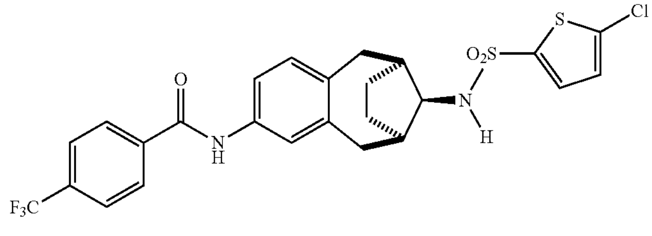 | 1 |

TABLE 3-continued

In vitro inhibition of γ-secretase activity for Sulfonamide-Based Compounds

| Compound | Chemical Structure | IC$_{50}$ (μM) |
|---|---|---|
| 11 | 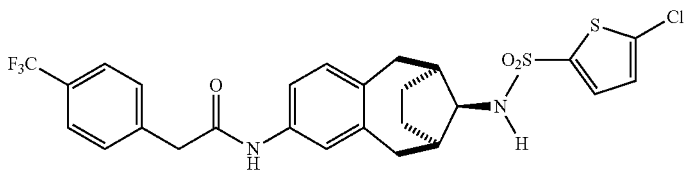 | 0.8 |
| 19 | 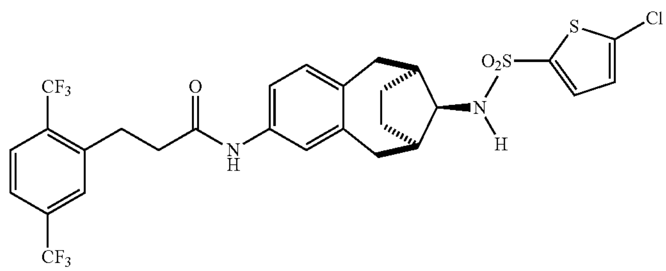 | 630 |
| 25 | 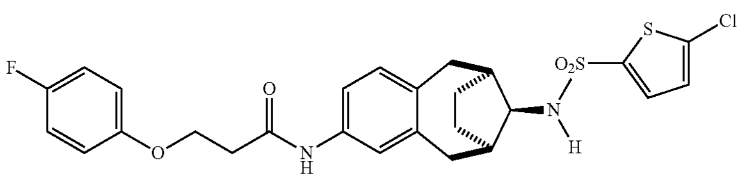 | 20 |
| (trans)-31 | 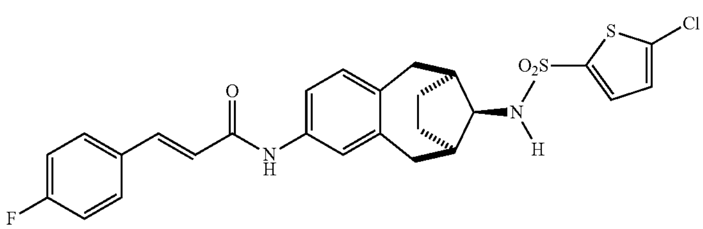 | 84 |
| (trans)-35 | 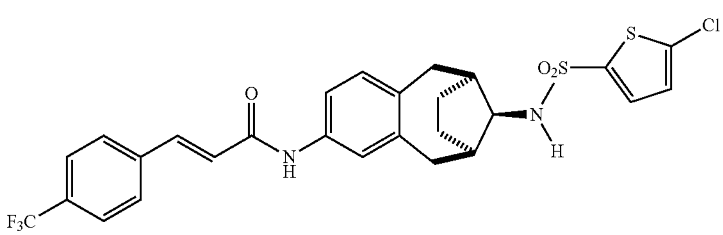 | 200 |
| 165 | 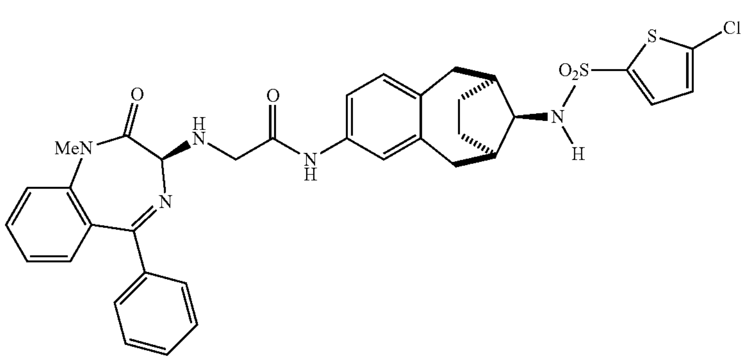 | 800 |

What is claimed is:

1. A method for treating a cancer selected from the group consisting of brain cancer, leukemia, bone and connective tissue sarcomas, breast cancer, adrenal cancer, thyroid cancer, pancreatic cancer, pituitary cancer, eye cancer, vaginal cancer, vulvar cancer, cervical cancer, uterine cancer, ovarian cancer, esophageal cancer, stomach cancer, colon cancer, rectal cancer, liver cancer, gallbladder cancer, cholangiocarcinomas, lung cancer, testicular cancer, prostate cancer, penile cancer, oral cancer, basal cancer, salivary gland cancer, pharynx cancer, skin cancer, kidney cancer, Wilms' tumor, bladder cancer, myxosarcoma, osteogenic sarcoma, endotheliosarcoma, lymphangioendotheliosarcoma, mesothelioma, synovioma, hemangioblastoma, epithelial carcinoma, cystadenocarcinoma, bronchogenic carcinoma, sweat gland carcinoma, sebaceous gland carcinoma, or papillary carcinoma and papillary adenocarcinomas, comprising administering to a subject in need of treatment of the cancer an effective amount of a compound of Formula I, having any one of the following structures:

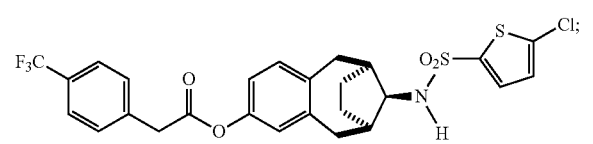

or a pharmaceutically acceptable salt thereof.

2. A method for treating a cancer, wherein the cancer is selected from the group consisting of brain cancer, leukemia, bone and connective tissue sarcomas, breast cancer, adrenal cancer, thyroid cancer, pancreatic cancer, pituitary cancer, eye cancer, vaginal cancer, vulvar cancer, cervical cancer, uterine cancer, ovarian cancer, esophageal cancer, stomach cancer, colon cancer, rectal cancer, liver cancer, gallbladder cancer, cholangiocarcinomas, lung cancer, testicular cancer, prostate cancer, penile cancer, oral cancer, basal cancer, salivary gland cancer, pharynx cancer, skin cancer, kidney cancer, Wilms' tumor, bladder cancer, myxosarcoma, osteogenic sarcoma, endotheliosarcoma, lymphangioendotheliosarcoma, mesothelioma, synovioma, hemangioblastoma, epithelial carcinoma, cystadenocarcinoma, bronchogenic carcinoma, sweat gland carcinoma, sebaceous gland carcinoma, or papillary carcinoma and papillary adenocarcinomas, comprising administering to a subject in need of treatment of the cancer an effective amount of a compound of Formula IIaa having the structure:

or a pharmaceutically acceptable salt thereof.

3. A method for treating a neurodegenerative disease, comprising administering to a subject in need of treatment or prevention of the neurodegenerative disease an effective amount of a compound of Formula I Formula I or a pharmaceutically acceptable salt thereof, wherein:
X is H, halo, $C_1$-$C_6$ alkyl, $C_1$-$C_6$ haloalkyl, $C_1$-$C_6$ alkoxy, or cyano;
each $R^1$ is independently H, halo, $C_1$-$C_6$ alkyl, $C_1$-$C_6$ haloalkyl, $C_1$-$C_6$ alkoxy, or cyano;
$R^2$ is each $R^3$ is independently H, halo, $C_1$-$C_6$ alkyl, $C_1$-$C_6$ haloalkyl, $C_1$-$C_6$ alkoxy, or cyano;
$Z^1$ is NH, O, or $CH_2$;
$Z^2$ is —($C_1$-$C_6$ alkylene)-, —($C_2$-$C_6$ alkenylene)-, or —(O—($C_2$-$C_6$ alkylene))-;
m is 3;
n is 1;
p is an integer from 1 to 5;
q is 0 or 1; and
v is an integer from 1 to 3.

4. The method of claim 3, wherein the compound of Formula I has the following Formula Iaa

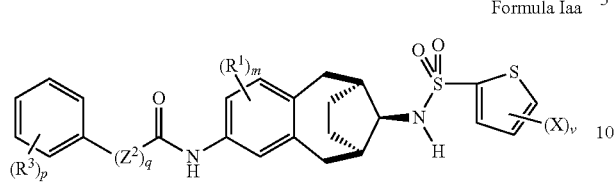

Formula Iaa wherein:

X is halo;

each $R^1$ is independently H, halo, $C_1$-$C_6$ alkyl, or $C_1$-$C_6$ haloalkyl; and each $R^3$ is independently H, halo, $C_1$-$C_6$ alkyl, or $C_1$-$C_6$ haloalkyl;

$Z^2$ is —($C_1$-$C_6$ alkylene)-, —($C_2$-$C_6$ alkenylene)-, or —(O—($C_2$-$C_6$ alkylene))-;

m is 3;

p is an integer from 1 to 5;

q is 0 or 1; and v is an integer from 1 to 3.

5. The method of claim 3, wherein each $R^1$ is H.

6. The method of claim 3, wherein v is 1 and X is in the 5-position of the thiopheno group.

7. The method of claim 3, wherein p is 1 and $R^3$ is in the 4-position of the phenyl group.

8. The method of claim 4, wherein the compound of Formula Iaa has the structure:

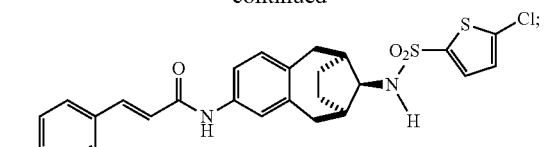

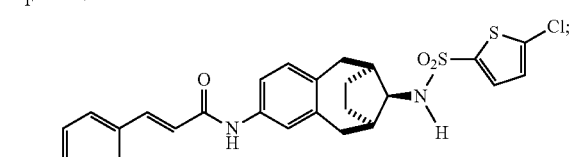

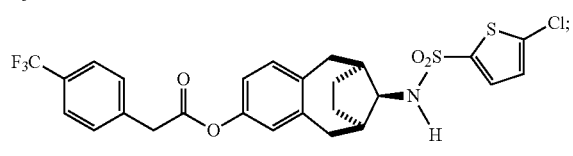

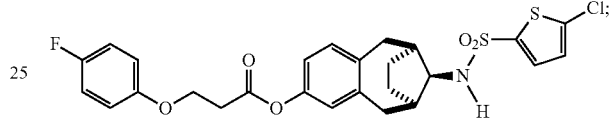

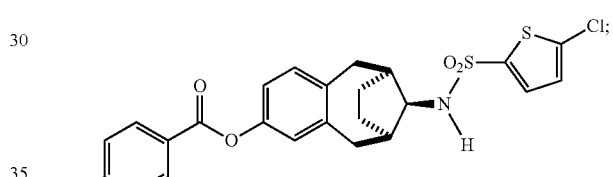

-continued

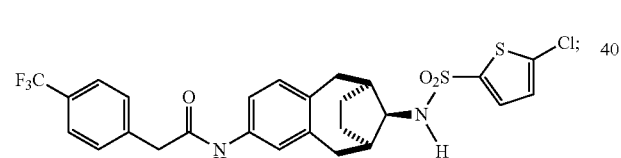

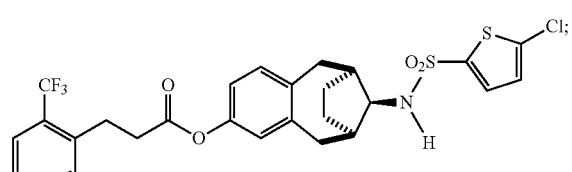

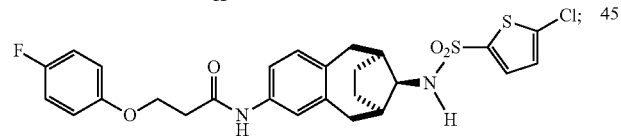

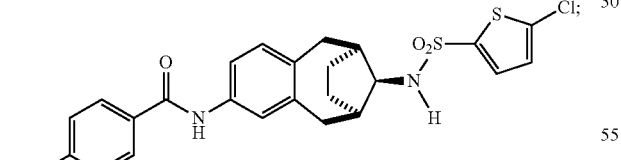

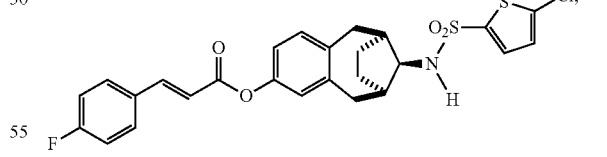

or a pharmaceutically acceptable salt thereof.

9. A method for treating a neurodegenerative disease, comprising administering to a subject in need of treatment of the neurodegenerative disease an effective amount of a compound of Formula II

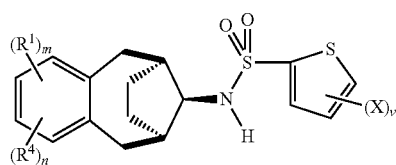

Formula II or a pharmaceutically acceptable salt thereof, wherein:
X is H, halo, $C_1$-$C_6$ alkyl, $C_1$-$C_6$ haloalkyl, $C_1$-$C_6$ alkoxy, or cyano;
each $R^1$ is independently H, halo, $C_1$-$C_6$ alkyl, $C_1$-$C_6$ haloalkyl, $C_1$-$C_6$ alkoxy, or cyano;
each $R^3$ is independently H, halo, $C_1$-$C_6$ alkyl, $C_1$-$C_6$ haloalkyl, $C_1$-$C_6$ alkoxy, or cyano;

$R^4$ is

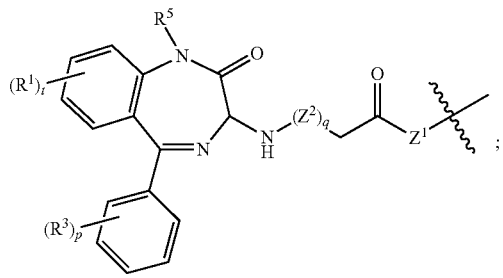

$R^5$ is H, $C_1$-$C_6$ alkyl, or $C_1$-$C_6$ haloalkyl;
$Z^1$ is NH, O, or $CH_2$;
$Z^2$ is —($C_1$-$C_6$ alkylene)- or —($C_2$-$C_6$ alkenylene)-;
m is 3;
n is 1;
p is 5;
t is 4;
q is 0 or 1; and
v is an integer from 1 to 3.

10. The method of claim 9, wherein the compound of Formula II has the following Formula IIa Formula IIa

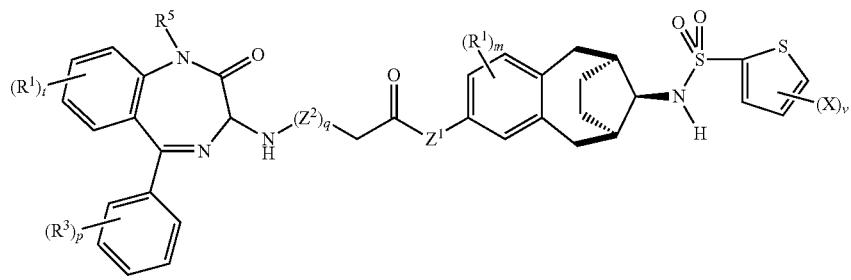

wherein:
X is H, halo, $C_1$-$C_6$ alkyl, $C_1$-$C_6$ haloalkyl, $C_1$-$C_6$ alkoxy, or cyano;
each $R^1$ is independently H, halo, $C_1$-$C_6$ alkyl, $C_1$-$C_6$ haloalkyl, $C_1$-$C_6$ alkoxy, or cyano;
each $R^3$ is independently H, halo, $C_1$-$C_6$ alkyl, $C_1$-$C_6$ haloalkyl, $C_1$-$C_6$ alkoxy, or cyano;
$R^5$ is H, $C_1$-$C_6$ alkyl, or $C_1$-$C_6$ haloalkyl;
$Z^1$ is NH, O or $CH_2$;
$Z^2$ is —($C_1$-$C_6$ alkylene)- or —($C_2$-$C_6$ alkenylene)-;
m is 3;
p is 5;
t is 4;
q is 0 or 1; and
v is an integer from 1 to 3.

11. The method of claim 10, wherein the compound of Formula IIa has the following Formula IIaa Formula IIa

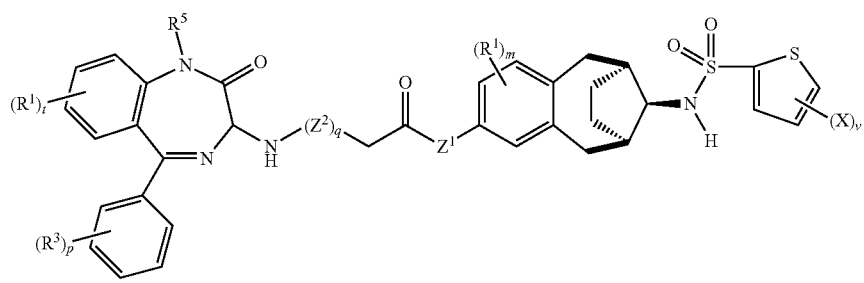

wherein:
X is halo;
each $R^1$ is independently H, halo, $C_1$-$C_6$ alkyl, or $C_1$-$C_6$ haloalkyl;
each $R^3$ is independently H, halo, $C_1$-$C_6$ alkyl, or $C_1$-$C_6$ haloalkyl;
$Z^2$ is —($C_1$-$C_6$ alkylene)- or —($C_2$-$C_6$ alkenylene)-;
m is 3;
p is 5;
t is 4;
q is 0 or 1; and
v is an integer from 1 to 3.

12. The method of claim 9, wherein each $R^1$ is H.
13. The method of claim 9, wherein $R^5$ is H or methyl.
14. The method of claim 9, wherein $R^5$ is methyl.
15. The method of claim 9, wherein q is 0.
16. The method of claim 9, wherein v is 1 and X is in the 5-position of the thiopheno group.
17. The method of claim 11, wherein the compound of Formula IIaa has the structure:

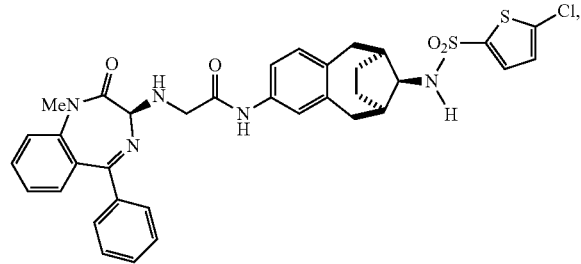

or a pharmaceutically acceptable salt thereof.

18. The method of claim 11, wherein the compound of Formula IIaa has the structure:

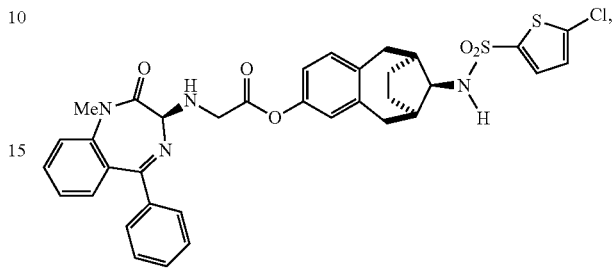

or a pharmaceutically acceptable salt thereof.

19. The method of claim 9, wherein the neurodegenerative disease is Alzheimer's disease, Parkinson's disease, ALS, or MS.
20. The method of claim 9, wherein the neurodegenerative disease is Alzheimer's disease.

* * * * *